US005811449A

United States Patent [19]
Medford et al.

[11] Patent Number: 5,811,449
[45] Date of Patent: *Sep. 22, 1998

[54] TREATMENT FOR ATHEROSCLEROSIS AND OTHER CARDIOVASCULAR AND INFLAMMATORY DISEASES

[75] Inventors: Russell M. Medford; R. Wayne Alexander; Sampath Parthasarathy, all of Atlanta; Bobby V. Khan, Dunwoody, all of Ga.

[73] Assignee: Emory University, Altanta, Ga.

[ * ] Notice: The term of this patent shall not extend beyond the expiration date of Pat. No. 5,380,747.

[21] Appl. No.: 483,335

[22] Filed: Jun. 7, 1995

Related U.S. Application Data

[60] Division of Ser. No. 317,399, Oct. 4, 1994, which is a continuation-in-part of Ser. No. 240,858, May 10, 1994, abandoned, which is a continuation-in-part of Ser. No. 969,934, Oct. 30, 1992, Pat. No. 5,380,747.

[51] Int. Cl.$^6$ .......................... A61K 31/40; A61K 31/54; A61K 31/265; A61K 31/185
[52] U.S. Cl. .......................... 514/423; 514/863; 530/331; 548/431; 548/531; 549/10; 558/230; 558/234; 558/235; 558/250; 562/26; 562/27; 564/76
[58] Field of Search .......................... 424/9.1, 9.2; 436/71, 436/86, 129; 514/18, 423, 478, 479, 484, 485, 487, 488, 489, 506, 513, 824, 825, 826, 861, 863; 530/331; 548/431; 558/230, 235; 564/76; 568/21, 25

[56] References Cited

U.S. PATENT DOCUMENTS

| | | | |
|---|---|---|---|
| 3,875,170 | 4/1975 | Montsumoto et al. | 260/293.69 |
| 4,056,621 | 11/1977 | Brown et al. | 424/273 R |
| 4,112,104 | 9/1978 | Durant et al. | 424/270 |
| 4,522,811 | 6/1985 | Eppstein et al. | 514/2 |
| 4,670,471 | 6/1987 | Clark | 514/724 |
| 4,868,116 | 9/1989 | Morgan et al. | 435/240.2 |
| 4,870,101 | 9/1989 | Ku et al. | 514/476 |
| 4,900,750 | 2/1990 | Archibold et al. | 514/335 |
| 4,980,286 | 12/1990 | Morgan et al. | 435/172.3 |
| 5,035,878 | 7/1991 | Borch et al. | 424/10 |
| 5,166,133 | 11/1992 | Houston et al. | 514/8 |
| 5,206,264 | 4/1993 | Marangus | 514/483 |
| 5,306,724 | 4/1994 | Goldberg | 514/369 |
| 5,380,747 | 1/1995 | Medford et al. | 514/423 |

FOREIGN PATENT DOCUMENTS

| | | | |
|---|---|---|---|
| 0 284 879 | 10/1988 | European Pat. Off. | A61K 31/145 |
| WO 93/01286 | 1/1993 | WIPO | C12N 15/11 |
| WO 93/01839 | 2/1993 | WIPO . | |
| WO 94/09772 | 5/1994 | WIPO | A61K 31/325 |
| WO 95/30415 | 11/1995 | WIPO | A61K 31/21 |

OTHER PUBLICATIONS

Kurzawa and Puacz, "Determination of the stability of sodium tetramethylene dithiocarbamate in dilute aqueous solutions by means of the sodium azide–iodine reaction," *Chem. Analy.* (Warsaw), 23(3):417–20 (1978) (Chemical Abstracts #205007s, 89:475 (1978)).

Martindale, "Disulfiram and Citrated Calcium Carbimide," *The Extra Pharmacopoeia,* 28th Edition, p. 579 (1985).
Neish, et al., "Functional Analysis of the Human Vascular Cell Adhesion Molecule 1 Promoter," *J. Exp. Med.,* 176:1583–1593 (1992).
Renoux, "Imuthiol., ®," *Marker Proteins Inflammation,* (Proceedings of the Third Symposium, Lyon, France, Jun. 26–28, 1985) 3:591–597 (Editors J. Bienvenu, et al.; Publisher, Walter de Gruyter, Berlin–New York, 1986).
Thorn and Ludwig, *The Dithiocarbamates and Related Compounds,* pp. 1–298 (Publisher, Elsevier Publishing Company, Amsterdam, New York, 1962).
Ueyama, "Advancements in plant pharmacology of dithiocarbamates," *Bochu Kagaku,* 32(1):11–19 (1967) (Chemical Abstracts #34892g, 69:3245 (1968)).
Renoux, G. "Imuthiol" *Marker Proteins Inflammation* (1986) 3 591–7 cited in Chem Abst. 105:183615.
Agrawal, et al., "Oligodeoxynucleoside phosphoramidates and phosphorothioates as inhibitors of human immunodeficiency virus," *Proc. Natl. Acad. Sci. USA,* 85:7079–7083 (1988).
Alvarez, D.E.M.J., R. Montoro, et al. (1986), "Determination of cadmium, copper, and lead in sodium chloride food salts by flame atomic absorption spectroscopy," *J. Assoc. Off. Anal. Chem.* 68(5):871–3.
Baselt, R.C., F.W.J. Sunderman, et al. (1977), "Comparisons of antidotal efficacy of sodium diethyldithiocarbamate, D–penicillamine an triethylenetetramine upon acute toxicity of nickel carbonyl in rats," *Res. Commun. Chem. Pathol. Pharmacol.* 18(4):677–88.
Biorkhem, I.F., A. Henriksson, et al. (1991), "The antioxidant butylated hydroxytoluene protects against atherosclerosis," *Arterioscler. Thromb.* 11(1):15–22.
Blume, et al., "Triple helix formation by purine–rich oligonucleotides targeted to the human dihydrofolate reductase promoter," *Nucl. Acids. Res.,* 20:1777–1784 (1992).
Brown and Langer, "Transdermal Delivery of Drugs," *Annual Review of Medicine,* 39:221–229 (1988).

(List continued on next page.)

*Primary Examiner*—Peter O'Sullivan
*Attorney, Agent, or Firm*—Sherry M. Knowles; Jacqueline Haley; King & Spalding

[57] ABSTRACT

A method for the treatment of cardiovascular diseases and noncardiovascular inflammatory diseases that are mediated by VCAM-1 is provided that includes the removal, decrease in the concentration of, or prevention of the formation of oxidized polyunsaturated fatty acids, or interferes with a complex formed between a polyunsaturated fatty acid or an oxidized polyunsaturated fatty acid and a protein or peptide that mediates the expression of VCAM-1. A method is also provided for suppressing the expression of a redox-sensitive gene or activating a gene that is suppressed through a redox-sensitive pathway, that includes administering an effective amount of a substance that prevents the oxidation of the oxidized signal, and typically, the oxidation of a polyunsaturated fatty acid, or interferes with a complex formed between the oxidized signal and a protein or peptide that mediates the expression of the redox gene.

9 Claims, 16 Drawing Sheets

OTHER PUBLICATIONS

Carew, T.E., D.C. Schwenke, et al., (1987), "Antiatherogenic effect of probucol unrelated to its hypocholesterolemic effect: evidence that antioxidants in vivo can selectively inhibit low density lipoprotein degradation in macrophage–rich fatty streaks and slow the progression of atherosclerosis in the Wantanabe heritable hyperlipidemic rabbit," Proc. Natl. Acad. Sci. U.S.A. 84(21):7725–9.

Cooney, et al., "Site–Specific Oligonucleotide Binding Represses Transcription of the Human c–myc Gene in Vitro," Science, 241:456–459 (1988).

Corke, C.F., (1984) "The influence of diethyl–dithiocarbamate ('Imuthiol') on mononuclear cells in vitro," Int. J. Immunoparmacol. 6(3):245–7.

Crooke, "Progress toward oligonucleotide therapeutics: pharmacodynamic properties," FASEB J., 7:533–539 (1993).

Cybulsky, et al., "Endothelial Expression of a Mononuclear Leukocyte Adhesion Molecule During Atherogenesis," Science, 251:788–791 (1991).

Donner, M., P.K. Husgafvel, et al. (1983), "Mutagenicity of rubber additives and curing fumes. Results from five short–term bioassays," Scand. J. Work Environ. Health 9(2):27–37.

Duval–Valentin, et al., "Specific inhibition of transcription by triple helix–forming oligonucleotides," Proc. Natl. Acad. Sci. USA, 89:504–508 (1992).

Eltaveb, M.A. and G.R.E. Van (1990), "Iron, copper, zinc and lead in hair from Sudanese populations of different age groups," Sci. Total Environ. 95:157–65.

Evans, R.G., J. Nielsen, et al. (1983), "Enhancement of heat sensitivity and modification of repair of potentially lethal heat damage in plateau–phase cultures of mammalian cells by diethyldithiocarbamate," Radiat. Res. 93(2):319–25.

Fishbein, L. (1976), "Environmental health aspects of fungicides. I. Dithiocarbamates," J. Toxicol. Environ. Health 1(5):713–35.

Fishbein, L. (1978), "Overview of potential mutagenic problems posed by some pesticides and their trace impurities," Environ. Health Perspect. 27:125–31.

Fruebis, et al., "Evidence for a concerted reaction between lipid hydroperoxides and polypeptides," Proc. Natl. Acad. Sci. USA, 89:10588–10592 (1992).

Gale, G.R., A. B. Smith, et al., "Diethyldithiocarbamate in treatment of acute cadmium poisoning," Ann. Clin. Lab. Sci. 11(6):476–83 (1981).

Grigoriev, et al., "A Triple Helix–forming Oligonucleotide–Intercalator Conjugate Acts as a Transcriptional Repressor via Inhibition of NF kB Binding to Interleukin–2 Receptor Alpha–Regulatory Sequence," J. Biol. Chem., 267:3389–3395 (1992).

Hacker, M.P., W.B. Ershler, et al., "Effect of disulfiram (tetraethylthiuram disulfide) and diethyldithiocarbamate on the bladder toxicity and antitumor activity of cyclophosphamide in mice," Cancer Res 42(11):4490–4 (1982).

Hemavathy, K.C. and N. B. Krishnamurthy, "Cytogentic effects of Cuman L. a dithiocarbamate fungicide," Mutat. Res. 208(1):57–60 (1988).

Holt, et al., "An Oligomer Complementary to c–myc mRNA Inhibits Proliferation of HL–60 Promyelocytic Cells and Induces Differntiation," Mol. Cell. Biol., 8:963–973 (1988).

Hording, Merete, P.C., Gotzsche, et al., "Lack of immunomodulating effect of disulfiram on HIV Positive patients," J. Immunopharmac. 12(2):145–147 (1990).

Iademarco, et al., "Characterization of the Promoter for Vascular Cell Adhesion Molecule–1 (VCAM–1)," J. of Biol. Chem., 267(23):16323–16329 (1992).

Itakura, et al., "Synthesis and Use of Synthetic Oligonucleotides," Ann. Rev. Biochem., 53:323–356 (1984).

Inoue, K., M. Fukunaga, et al., "Effect of dislfiram and its reduced metabolite, diethyldithiocarbamate on aldehyde dehydrogenase of human erythrocytes," Life Sci. 30(5):419–24 (1982).

Jones, M.M. and M.G. Cherian, "The search for chelate antagonists for chronic cadmium intoxication," Toxicology 62(1):1–25 (1990).

Jones, S.G., M.A. Basinger, et al., "A comparison of diethyldithiocarbamate and EDTA as antidotes for acute cadmium intoxication," Res. Commun. Chem. Pathol. Pharmacol. 38(2):271–8 (1982).

Ku, G., N.S. Doherty, et al., "Ex vico lipopolysaccharide–induced interleukin–1 secretion from murine peritoneal macrophages inbhibited by probucol, a hypocholesterolemic agent with *antioxidant* proprieties," Faseb J. 4(6):1645–53 (1990).

Lang, J.M., C. Trepo, et al., "Randomised, double–blind, placebo–controlled trial of ditocarb sodium ('Imuthiol') in human immunodeficiency virus infection," The Lancet Sep. 24, 1988:702–706 (1988).

Lemarie, E., M. Musset, et al.,"Clinical characterization of imuthiol," Methods Find Exp. Clin. Pharmacol. 8(1):51–4 (1986).

Lin, P.S., L. Kwock, et al., "Copper chelator enhancement of bleomycin cytotoxicity," Cancer 46(11):2360–4 (1980).

Maher, et al., "Inhibition of DNA Binding Proteins by Oligonucleotide–Directed Triple Helix Formation," Science, 245:725–730 (1989).

Marui, et al., "Vascular Cell Adhesion Molecule–1 (VCAM–1) Gene Transcription and Expression are Regulated Through an Antioxidant–Sensitive Mechanism in Human Vascular Endothelial Cells," J. of Clin. Invest., 92(4):1866–1874 (1993).

Menne, T. and K. Kaaber, "Treatment of pompholyx due to nickel allergy with chelating agents," Contact Dermatitis 4:(5):289–90 (1978).

Miller, D.B., "Neurotoxicity of the pesticidal carbamates," Neurobehay, Toxicol. Teratol. 4(6):779–87 (1982).

Moerlein, S.M., A. Daugherty, et al., "Utility of Tc–99m–and in–111–labelled low–density lipoprotein as radiopharmaceuticals for metabolic imaging," J. Nuclear Medicine 32:(1): 925–926 (1991).

Mulligan, "The Basic Science of Gene Therapy," Science 260:926–932 (1993).

Narang, et al., "Chemical Synthesis of Deoxyoligonucleotides by the Modified Triester Method," Methods Enzymol., 65:610–620 (1980).

Offensperger, et al., "In vivo inhibition of duck hepatitis B virus replication and gene expression by phosphorothioates modified antisense oligodeoxynucleotides," EMBO J., 12:1257–1262 (1993).

Orson, et al., "Oligonucleotide inhibition of IL2R Alpha mRNA transcription by promoter region collinear triplex formation in lymphocytes," Nucl. Acids Res., 19:3435–3441 (1991).

Pages, A., J.S. Casas, et al., "Dithiocarbamates in heavy metal poisoning: complexes of N,N–di(2–hidroxyethyl)dithiocarbamate with Zn(II), Cd(II), Hg(II), CH3Hg(II), and C6H5Hg(II)." J. Inorg. Biochem. 25(1):35–42 (1985).

Paller, M.S., J.R. Hoidal, et al., "Oxygen fee Radicals in Ischemic acute renal failure in the rat," *J. Clin. Invest.* 74:1156–1164 (1984).

Parthasarathy, S., S.G. Young, et al., "Probucol inhibits exidative modification of low density lipoprotein," *J. Clin. Invest.* 77(2):641–4 (1986).

Pasgualini, et al., "Brain–tropic Radiopharmaceutical Compounds Comprising a Transition Metal Nitride Complex, and Preparation Method Therefor," Chemical Abstracts, 119:23788 (1993).

Perchellet, E.M., E.A. Maatta, et al., "Effects of Diverse Intracellular Thiol Delivery Agents on Glutathione Peroxidase Activity, the Ratio of Reduced/Oxidized Glutathione, and Ornithine Decarboxylase Induction in Isolated Mouse Epidermal Cells Treated with 12–O–Tetradecanoylphorbol–13–Acetate." *J. Cell. Physiol.* 131:64–73 (1987).

Perkins, et al., "Distinct Combinations of NF–KAPPA B Subunits Determine the Specificity of Transcriptional Activation," *Proc. Natl. Acad. Sci. USA*, 89:1529–1533 (1992).

Pober, J.S. and R.S. Cotran, "What can be learned from the expression of endothelial adhesioin molecules in tussues? [Editorial]," *Lab. Invest.* 64:301–305 (1991).

Pompidou, A., M.C., Delsaux, et al., "Isoprinosine and Imuthiol. two potentially active compounds in patients with AIDS–related complex symptoms." *Cancer Res.* (1985).

Postel, et al., "Evidence that a triplex–forming oligodeoxyribonucleotide binds to the c–myc promoter in HeLa cells, thereby reducing c–myc mRNA levels," *Proc. Natl. Acad. Sci. USA*, 88:8227–8231 (1991).

Quinto, I. and M.E. De, "Evaluation of Propineb, a dithiocarbamate pesticide, in the mouse–sperm morphology assay," *Mutat. Res.* 124(3–4):235–40 (1983).

Rannug, A. and U. Rannug, "Enzyme inhibition as a possible mechanism of the mutagenicity of dithiocarbamic acid derivatives in *Salmonella typhimurium*," *Chem. Biol. Interact.* 49(3):329–40 (1984).

Reisinger, et al., "Inhibition of HIV progression by dithiocarb," *Lancet*, 335:679–682 (1990).

Renoux, G., "Characterization of immunotherapeutic agents: the example of imuthiol," *Methods Find. Exp. Clin. Pharmacol.* 8(1):45–50 (1986).

Renoux, G., "The cortex regulates the immune system and the activities of a T–cell specific immunopotentiator," *Int. J. Neurosci.* 39(1–2):177–87 (1988).

Renoux, M. J.P. Giroud, et al., "Early changes in immune parameters induced by an acute nonantigenic inflammation in mouse: influence of imuthiol," *Int. J. Immunopharmacol.* 8(1):107–17 (1986).

Rice, G.E., J.M. Munro, et al., "Vascular and nonvascular expression of INCAM–110. A target for mononuclear leukocyte adhesion in normal and inflamed human tissues." *Am. J. Pathol.* (1991).

Robinson, K.A., et al., "Effects of a Thiol Antioxidant on Leucocyte Adherence to Aortic Endothelium During Atherogenesis: Quantitative Sem Assessment," *Proc. 51st Annual Meeting of the Microscopy Society of America* (1993).

Sarah and Bors, "Radical reactions in vivo–an overview," *Radiat. Environ. Biophys.*, 29(4):249–262 (1990).

Sarin, et al., "Inhibition of acquired immunodeficiency syndrome virus by oligodeoxynucleoside methylphosphonates," *Proc. Natl. Acad. Sci. USA*, 85:7448–7794 (1989).

Schreck, R., P. Rieber, et al., "Reactive oxygen intermediates as apparently widely used messengers in the activation of the NF–kappa B transcription factor and HIC–1." *Embo J* 10(8):2247–58 (1991).

Schreck, R., B. Meier, et al., "Dithiocarbamates as Potent Inhibitors of Nuclear Factor kB Activation in Intact Cells," *J. Exp. Med.* 175:1181–1194 (1992).

Shaw, et al., "Modified deoxyoligonucleotides stable to exonuclease degradation in serum," *Nucl. Acids. Res.*, 19:747–750 (1991).

Steinberg, D., S. Parthasarathy, et al., "Beyond cholesterol: modification of low–density lipoprotein that increase its atherogenicity." *N. Engl. J. Med.* 320:915–924 (1989).

Steinberg, D. and W. Participants, "Antioxidants in the Prevention of Human Atherosclerosis," *Circulation* 85:2338–2344 (1992).

Sunderman, F.W., "Clinical response to *therapeutic* agents in poisoning from mercury vapor," *Ann. Clin. Lab. Sci.* 8(4):259–69 (1978).

Sunderman, F.W., "Efficacy of sodium diethyldithiocarbamate (dithiocarb) in acute nickel carbonyl poisoning," *Ann. Clin. Lab. Sci.* 9(1):1–10 (1979).

Tandon, S.K., N.S. Hashmi, et al., "The lead–chelating effects of substituted dithiocarbamates," *Biomed. Environ. Sci.* 3(3):299–305 (1990).

Tiwari, et al., "Possible Anti–Parkinsonian Compounds IV, Synthesis of Piperazne bis[amino(thiocarbonyl)thio–acetates and propionates]," Chemical Abstracts, 81(17):105447b (1974).

Topping, R.J. and M.M. Jones, "Optimal dithiocarbamate structure for immunomodulator action," *Med. Hypotheses* 27(1):55–7 (1988).

Tripathy, N.K., B. Maihi, et al., "Genotoxicity of ziram established through wing, eye and female germ–line mosaic assays and the sex–linked recessive lethal test in Drosophila melanogaster" *Mutat. Res.* 224(2):161–9 (1989).

Walker, et al., "Antipseudomonal Effects of Selected Dithiocarbamates Alone and in Combination with Gentamicin or Aztreonam," *Res. Comm. in Chem. Pathol. and Pharmacol.*, 63(1):101–117 (1989).

Warner, B.B., M.S. Burhans, et al., "Tumor necrosis factor–alpha increases Mn–SOD expression: protection against oxidant injury," *Am. J. Physiol.* (1991).

Wickstrom, et al., "Human promyelocytic leukemia HL–60 cell proliferation and c–myc protein expression are inhibited by an antisense pentadecadeoxynucleotide targeted against c–myc mRNA," *Proc. Natl. Acad. Sci. USA*, 85:1028–1032 (1988).

Young, et al., "Triple helix formation inhibits transcription elongation in vitro," *Proc. Natl. Acad. Sci. USA*, 88:10023–10026 (1991).

Zamecnik, et al., "Inhibition of Rous sarcoma virus replication and cell transformation by a specific oligodeoxynucleotide," *Proc. Natl. Acad. Sci. USA*, 75:280–284 (1978).

Zamecnik, et al., "Inhibition of replication and expression of human T–cell lymphotropic virus type III in cultured cells by exogenous synthetic oligonucleotides complementary to viral RNA," *Proc. Natl. Acad. Sci. USA*, 83:4143–4146 (1986).

Zhu, et al., "Systemic Gene Expression After Intravenous DNA Delivery into Adult Mice," *Science*, 261:209–211 (1993).

*The Merck Index*, Merck & Co., Rahway, NJ, Eleventh Edition, p. 533 (1989).

C: Control
T: TNFα (100 U/ml)
L: Linoleic Acid (7.5 μM)

C: Control
T: TNFα (100 U/ml)
L: Linoleic Acid (7.5 μM)

FIGURES 9a & 9b   * – VALUE DIFFERS (p<0.05) FROM CONTROL
– VALUE DIFFERS (p<0.05) FROM RESPECTIVE FATTY ACID NOT TREATED WITH PDTC

VCAM-1

E-SELECTIN

ICAM-1

VCAM-1

FIG. 17

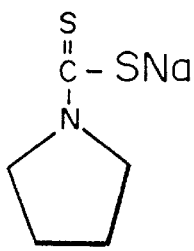

SODIUM PYRROLIDINE-N-CARBODITHIOATE

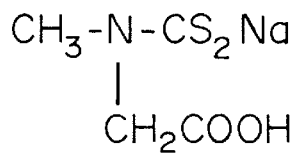

SODIUM-N-METHYL-N-CARBOXYMETHYL-N-CARBODITHIOATE
(OR SODIUM SARCOSINEDITHIOCARBAMATE)

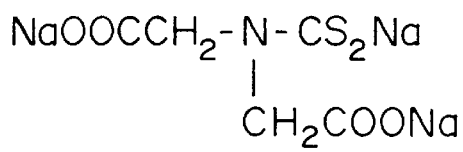

TRISODIUM N,N-di(CARBOXYMETHYL)-N-CARBODITHIOATE
(OR IMINODIACETIC ACID DITHIOCARBAMATE, TRISODIUM)

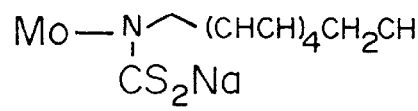

SODIUM N-METHYL-D-GLUCAMINE-N-CARBODITHIOATE

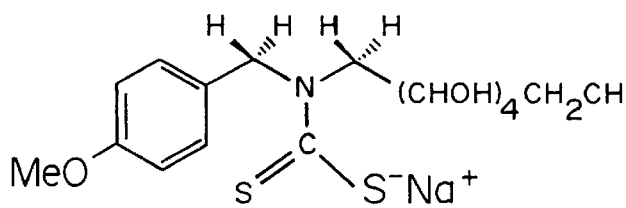

SODIUM N-(4-METHOXYBENZYL)-D-GLUCAMINE-N-CARBODITHIOATE

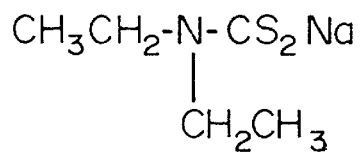

SODIUM N,N-DIETHYL-N-CARBODITHIOATE (OR SODIUM DIETHYLDITHIOCARBAMATE)

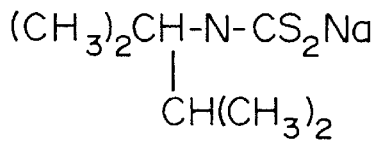

SODIUM N,N-DIISOPROPYL-N-CARBODITHIOATE
(OR SODIUM DIISOPROPYLDITHIOCARBAMATE)

(1 MICROMOL OF 13-HPODE WAS INCUBATED WITH 200 MICROGRAMS OF BSA IN THE PRESENCE OF PDTC FOR 6 DAYS. FLUORESCENCE WAS MEASURED AT 430-460 nm WITH EXCITATION SET AT 330-360 nm)

EFFECT OF PDTC ON THE FORMATION OF FLUORESCENT ADDUCTS FROM BSA AND LOOH 1. 0 PDTC
2. 1 µM PDTC
3. 2.5 µM PDTC
4. 5 µM PDTC

EFFECT OF PDTC ON THE OXIDATION OF LDL BY HRP

| Cells | Linoleic | Ox-linoleic |
|---|---|---|
| Control | 9561 | 11445 |
| TNFα | 8874 | 27894 |
| IL-1β | 9134 | 25813* |
| TNFα +PDTC | 8444 | 7966# |
| IL-1β +PDTC | 8257 | 8012# |

\* - value differs (p<0.05) from Control
\# - value differs (p<0.05) from corresponding group not treated with PDTC

TREATMENT FOR ATHEROSCLEROSIS AND OTHER CARDIOVASCULAR AND INFLAMMATORY DISEASES

This application is a divisional application of U.S. Ser. No. 08/317,399, filed Oct. 4, 1994, which is a continuation-in-part of U.S. Ser. No. 08/240,858, now abandoned filed on May 10, 1994 by Russell M. Medford, Margaret K. Offermann, Wayne R. Alexander, and Sampath Parthasarathy entitled "Treatment of Atherosclerosis and Other Cardiovascular and Inflammatory Diseases," which is a continuation-in-part of U.S. Ser. No. 07/969,934, filed on Oct. 30, 1992 by Russell M. Medford, Margaret K. Offermann, and R. Wayne Alexander, entitled "Treatment of Atherosclerosis and Other Cardiovascular and Inflammatory Diseases," now U.S. Pat. No. 5,380,747.

The U.S. government may have rights in this invention by virtue of a grant from the National Institutes of Health that partially funded work leading to the invention.

BACKGROUND OF THE INVENTION

This application is in the area of methods and compositions for the treatment of atherosclerosis and other cardiovascular and inflammatory diseases.

Adhesion of leukocytes to the endothelium represents a fundamental, early event in a wide variety of inflammatory conditions, including atherosclerosis, autoimmune disorders and bacterial and viral infections. Leukocyte recruitment to the endothelium is started when inducible adhesion molecule receptors on the surface of endothelial cells interact with counterreceptors on immune cells. Vascular endothelial cells determine which type of leukocytes (monocytes, lymphocytes, or neutrophils) are recruited, by selectively expressing specific adhesion molecules, such as vascular cell adhesion molecule-1 (VCAM-1), intracellular adhesion molecule-1 (ICAM-1), and E-selectin. In the earliest stage of the atherosclerotic lesion, there is a localized endothelial expression of VCAM-1 and selective recruitment of mononuclear leukocytes that express the integrin counterreceptor VLA-4. Because of the selective expression of VLA-4 on monocytes and lymphocytes, but not neutrophils, VCAM-1 is important in mediating the selective adhesion of mononuclear leukocytes. Subsequent conversion of leucocytes to foamy macrophages results in the synthesis of a wide variety of inflammatory cytokines, growth factors, and chemoattractants that help propagate the leukocyte and platelet. recruitment, smooth muscle cell proliferation, endothelial cell activation, and extracellular matrix synthesis characteristic of maturing atherosclerotic plaque.

VCAM-1 is expressed in cultured human vascular endothelial cells after activation by lipopolysaccharide (LPS) and cytokines such as interleukin-1 (IL-1) and tumor necrosis factor (TNF-α). These factors are not selective for activation of cell adhesion molecule expression.

Molecular analysis of the regulatory elements on the human VCAM-1 gene that control its expression suggests an important role for nuclear factor-kB (NF-kB), a transcriptional regulatory factor, or an NF-kβ like binding protein in oxidation-reduction-sensitive regulation of VCAM-1 gene expression. Transcriptional factors are proteins that activate (or repress) gene expression within the cell nucleus by binding to specific DNA sequences called "enhancer elements" that are generally near the region of the gene, called the "promoter," from which RNA synthesis is initiated. Nuclear factor-kB is a ubiquitously expressed multisubunit transcription factor activated in several cell types by a large and diverse group of inflammatory agents such as TNFα, IL-Lβ, bacterial endotoxin, and RNA viruses. It plays a key role in mediating inflammatory and other stress signals to the nuclear regulatory apparatus. Although the precise biochemical signals that activate NF-kB are unknown, this transcriptional factor may integrate into a common molecular pathway many of the risk factors and "causative" signals of atherosclerosis, such as hyperlipidemia, smoking, hypertension, and diabetes mellitus.

Importantly, the activation of NF-kB in vascular endothelial cells by diverse signals can be specifically hinhibited by antioxidants such as N-acetylcysteine and pyrrolidine dithiocarbamate (see U.S. Ser. No. 07/969,934, now allowed). This has led to the hypothesis that oxygen radicals play an important role in the activation of NF-kB through an undefined oxidation-reduction mechanism. Because an NF-kB-like enhancer element also regulates the transcription of the VCAM-1 promoter in an oxidation-reduction-sensitive manner, oxidative stress in the atherosclerotic lesion may play a role in regulating VCAM-1 gene expression through this oxidation-reduction-sensitive transcriptional regulatory protein.

It has been hypothesized that modification of low-density lipoprotein (LDL) into oxidatively modified LDL (ox-LDL) by reactive oxygen species is the central event that initiates and propagates atherosclerosis. Steinberg, et al., *N. Engl. J. Med.* 1989; 320:915–924. Oxidized LDL is a complex structure consisting of at least several chemically distinct oxidized materials, each of which, alone or in combination, may modulate cytokine-activated adhesion molecule gene expression. Fatty acid hydroperoxides such as linoleyl hydroperoxide (13-HPODE) are produced from free fatty acids by lipoxygenases and are an important component of oxidized LDL.

It has been proposed that a generation of oxidized lipids is formed by the action of the cell lipoxygenase system and that the oxidized lipids are subsequently transferred to LDL. There is thereafter a propagation reaction within the LDL in the medium catalyzed by transition metals and/or sulfhydryl compounds Previous investigations have demonstrated that fatty acid modification of cultured endothelial cells can alter their susceptibility to oxidant injury. Supplementation of saturated or monounsaturated fatty acids to cultured endothelial cells reduces their susceptibility to oxidant injury, whereas supplementation with polyunsaturated fatty acids (PUFA) enhances susceptibility to oxidant injury.

Using reverse-phase HPLC analysis of native and saponified lipid extracts of LDL, it has been demonstrated that 13-HPODE is the predominant oxidized fatty acid in LDL oxidized by activated human monocytes. Chronic exposure to oxidized LDL provides an oxidative signal to vascular endothelial cells, possibly through a specific fatty acid hydroperoxide, that selectively augments cytokine-induced VCAM-1 gene expression.

Through a mechanism that is not well defined, areas of vessel wall predisposed to atherosclerosis preferentially sequester circulating LDL. Through a poorly understood pathway, endothelial, smooth muscle, and/or inflammatory cells then convert LDL to ox-LDL. In contrast to LDL, which is taken up through the LDL receptor, monocytes avidly take up ox-LDL through a "scavenger" receptor whose expression, unlike the LDL receptor, is not inhibited as the content of intracellular lipid rises. Thus, monocytes continue to take up ox-LDL and become lipid-engorged macrophage-foam cells that form the fatty streak.

Given that cardiovascular disease is currently the leading cause of death in the United States, and ninety percent of cardiovascular disease is presently diagnosed as atherosclerosis, there is a strong need to identify new methods and pharmaceutical agents for its treatment. Important to this goal is the identification and manipulation of the specific oxidized biological compounds that act as selective regulators of the expression of mediators of the inflammatory process, and in particular, VCAM-1. A more general goal is to identify selective methods for suppressing the expression of redox sensitive genes or activating redox sensitive genes that are suppressed.

It is therefore an object of the present invention to provide a treatment for atherosclerosis and other cardiovascular and inflammatory diseases.

It is another object of the present invention to provide a method for the selective inhibition of VCAM-1.

It is still another object of the present invention to provide a method for the treatment of a human disease or disorder that is mediated by the expression or suppression of a redox sensitive gene.

It is another object of the present invention to provide pharmaceutical compositions for the treatment of atherosclerosis and other cardiovascular and inflammatory diseases.

SUMMARY OF THE INVENTION

It has been discovered that polyunsaturated fatty acids ("PUFAs") and their hydroperoxides ("ox-PUFAs"), which are important components of oxidatively modified low density lipoprotein (LDL), induce the expression of VCAM-1, but not intracellular adhesion molecule-1 (ICAM-1) or E-selectin in human aortic endothelial cells, through a mechanism that is not mediated by cytokines or other noncytokine signals. This is a fundamental discovery of a an important and previously unknown biological pathway in VCAM-1 mediated immune responses.

As nonlimiting examples, linoleic acid, linolenic acid, arachidonic acid, linoleyl hydroperoxide (13-HPODE) and arachidonic hydroperoxide (15-HPETE) induce cell-surface gene expression of VCAM-1 but not ICAM-1 or E-selectin. Saturated fatty acids (such as stearic acid) and monounsaturated fatty acids (such as oleic acid) do not induce the expression of VCAM-1, ICAM-1, or E-selectin.

The induction of VCAM-1 by PUFAs and their fatty acid hydroperoxides is suppressed by the antioxidant pyrrolidine dithiocarbamate (PDTC). This indicates that the induction is mediated by an oxidized signal molecule, and that the induction is prevented when the oxidation of the molecule is blocked (i.e., the oxidation does not occur), reversed (i.e., the signal molecule is reduced), or when the redox modified signal is otherwise prevented from interacting with its regulatory target.

Cells that are chronically exposed to higher than normal levels of polyunsaturated fatty acids or their oxidized counterparts can initiate an immune response that is not normal and which is out of proportion to the threat presented, leading to a diseased state. The oversensitization of vascular endothelial cells to PUFAS and ox-PUFAS can accelerate the formation, for example, of atherosclerotic plaque.

Based on these discoveries, a method for the treatment of atherosclerosis, post-angioplasty restenosis, coronary artery diseases, angina, and other cardiovascular diseases, as well as noncardiovascular inflammatory diseases that are mediated by VCAM-1, is provided that includes the removal, decrease in the concentration of, or prevention of the formation of oxidized polyunsaturated fatty acids including but not limited to oxidized linoleic ($C_{18}\Delta^{9,12}$), linolenic ($C_{18}\Delta^{6,9,12}$), arachidonic ($C_{20}\Delta^{5,8,11,14}$) and eicosatrienoic ($C_{20}\Delta^{8,11,14}$) acids. Nonlimiting examples of noncardiovascular inflammatory diseases that are mediated by VCAM-1 include rheumatoid and osteoarthritis, asthma, dermatitis, and multiple sclerosis.

This method represents a significant advance in treating cardiovascular disease, in that it goes beyond the current therapies designed simply to inhibit the progression of the disease, and when used appropriately, provides the possibility to medically "cure" atherosclerosis by preventing new lesions from developing and causing established lesions to regress.

In an alternative embodiment, a method is provided for suppressing the expression of a redox-sensitive gene or activating a gene that is suppressed through a redox-sensitive pathway, that includes administering an effective amount of a substance that prevents the oxidation of the oxidized signal, and typically, the oxidation of a polyunsaturated fatty acid. Representative redox-sensitive genes that are involved in the presentation of an immune response include, but are not limited to, those expressing cytokines involved in initiating the immune response (e.g., IL-1β), chemoattractants that promote the migration of inflammatory cells to a point of injury (e.g., MCP-1), growth factors (e.g., IL-6 and the thrombin receptor), and adhesion molecules (e.g., VCAM-1 and E-selectin).

Screens for disorders mediated by VCAM-1 or a redox-sensitive gene are also provided that include the quantification of surrogate markers of the disease. In one embodiment, the level of oxidized polyunsaturated fatty acid, or other appropriate markers, in the tissue or blood, for example, of a host is evaluated as a means of assessing the "oxidative environment" of the host and the host's susceptibility to VCAM-1 or redox-sensitive gene mediated disease.

In another embodiment, the level of circulating or cell-surface VCAM-1 or other appropriate marker and the effect on that level of administration of an appropriate antioxidant is quantified.

In yet another assay, the sensitization of a host's vascular endothelial cells to polyunsaturated fatty acids or their oxidized counterparts is evaluated. This can be accomplished, for example, by challenging a host with a PUFA or ox-PUFA and comparing the resulting concentration of cell-surface or circulating VCAM-1 or other surrogate marker to a population norm.

In another embodiment, in vivo models of atherosclerosis or other heart or inflammatory diseases that are mediated by VCAM-1 can be provided by administering to a host animal an excessive amount of PUFA or oxidized polyunsaturated fatty acid to induce disease. These animals can be used in clinical research to further the understanding of these disorders.

In yet another embodiment of the invention, compounds can be assessed for their ability to treat disorders mediated by VCAM-1 on the basis of their ability to inhibit the oxidation of a polyunsaturated fatty acid, or the interaction of a PUFA or ox-PUFA with a protein target.

This can be accomplished by challenging a host, for example, a human or an animal such as a mouse, to a high level of PUFA or ox-PUFA and then determining the therapeutic efficacy of a test compound based on its ability to decrease circulating or cell surface VCAM-1 concentration. Alternatively, an in vitro screen can be used that is based on the ability of the test compound to prevent the oxidation of a PUFA, or the interaction of a PUFA or ox-PUFA with a protein target in the presence of an oxidizing substance such as a metal, for example, copper, or an enzyme such as a peroxidase, lipoxygenase, cyclooxygenase, or cytochrome P450.

In another embodiment, vascular endothelial cells are exposed to TNF-α or other VCAM-1 inducing material for an appropriate time and then broken by any appropriate means, for example by sonication or freeze-thaw. The cytosolic and membrane compartments are isolated. Radiolabeled PUFA is added to defined amounts of the compartments. The ability of the liquid to convert PUFA to ox-PUFA in the presence or absence of a test compound is assayed. Intact cells can be used in place of the broken cell system.

BRIEF DESCRIPTION OF THE FIGURES

FIG. 13 indicates that multiple regulatory signals induce VCAM-1 but not ICAM-1 through a common, dithiocarbamate-sensitive pathway in human vascular endothelial cells.

FIG. 17 is an illustration of the chemical structures of the following active dithiocarbamates: sodium pyrrolidine-N-carbodithioate, sodium N-methyl-N-carboxymethyl-N-carbodithioate, trisodium N,N-di(carboxymethyl)-N-carbodithioate, sodium N-methyl-D-glucamine-N-carbodithioate, sodium N,N-diethyl-N-carbodithioate (sodium diethyldithiocarbamate), and sodium N,N-diisopropyl-N-carbodithioate.

DETAILED DESCRIPTION OF THE INVENTION

I. Definitions

Figure 1:
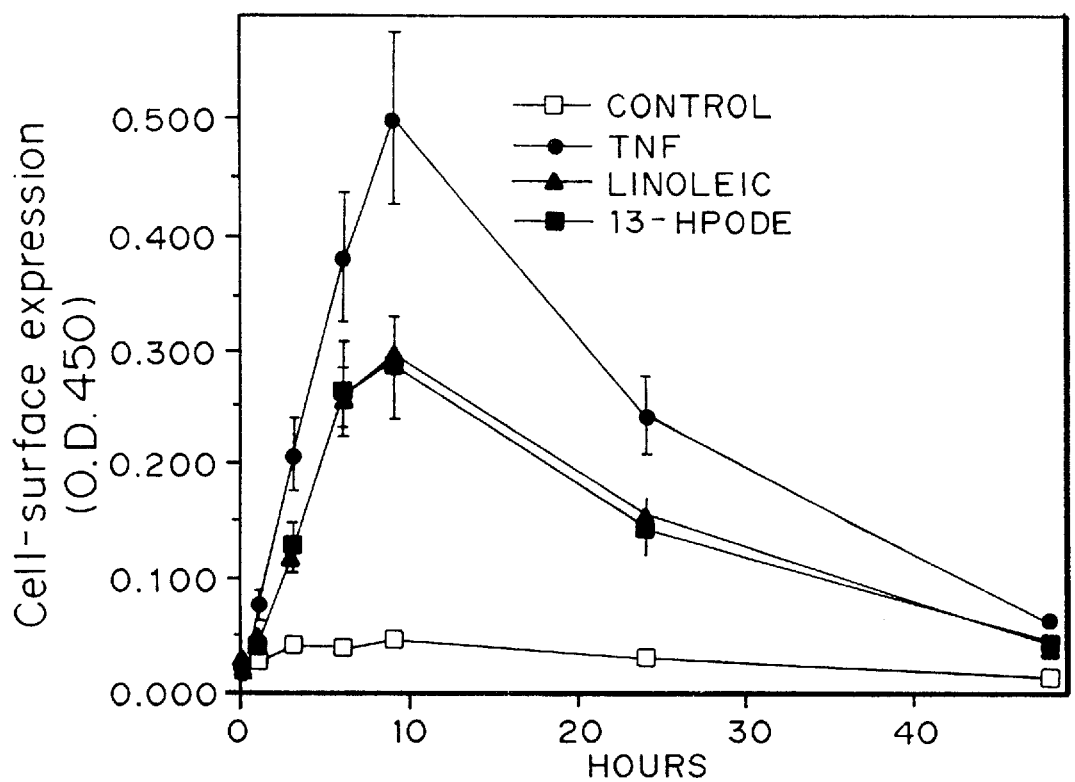
FIG. 1 is a graph of the cell-surface expression (O.D. 450 nm) of VCAM-1 as a function of hours in human aortic endothelial cells on exposure to the cytokine TNF-α (closed circle); linoleic acid (closed triangle); and linoleyl hydroperoxide (13-HPODE, closed square); and in the absence of exposure to these substances (control, open square).

As used herein, the term polyunsaturated fatty acid (also referred to herein as a "PUFA") refers to a fatty acid (typically $C_8$ to $C_{24}$) that has at least two alkenyl bonds, and includes but is not limited to linoleic ($C_{18}\Delta^{9,12}$), linolanic ($C_{18}\Delta^{6,9,12}$), arachidonic ($C_{20}\Delta^{5,8,11,14}$) and eicosatrienoic ($C_{20}\Delta^{8,11,14}$) acids.

The term oxidized polyunsaturated fatty acid refers to an unsaturated fatty acid in which at least one of the alkenyl bonds has been converted to a hydroperoxide of the structure. Nonlimiting examples are:

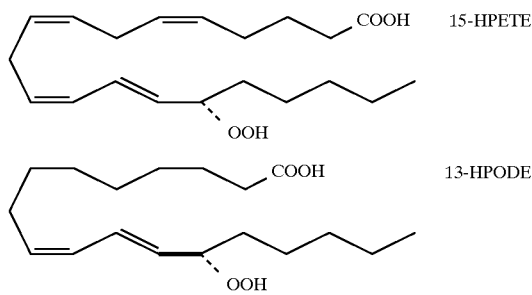

The term alkyl, as used herein, unless otherwise specified, refers to a saturated straight, branched, or cyclic (in the case of $C_5$ or greater) hydrocarbon of $C_1$ to $C_{10}$ (or lower alkyl, i.e., $C_1$ to $C_5$), which specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted on any of the carbons with one or more moieties selected from the group consisting of hydroxyl, amino, or mono- or disubstituted amino, wherein the substituent group is independently alkyl, aryl, alkaryl or aralkyl; aryl, alkoxy, aryloxy, nitro, cyano, sulfonic acid, sulfate, phosphonic acid, phosphate, or phosphonate, either unprotected, or protected as necessary, as known to those skilled in the art, for example, an taught in Greene, et al., "Protective Groups in organic Synthesis," John Wiley and Sons, Second Edition, 1991.

The term alkenyl, as referred to herein, and unless otherwise specified, refers to a straight, branched, or cyclic hydrocarbon of $C_2$ to $C_{10}$ with at least one double bond.

The term alkynyl, as referred to herein, and unless otherwise specified, refers to a $C_2$ to $C_{10}$ straight or branched hydrocarbon with at least one triple bond.

The term aralkyl refers to an aryl group with at least one alkyl substituent.

The term alkaryl refers to an alkyl group that has at least one aryl substituent.

The term halo (alkyl, alkenyl, or alkynyl) refers to an alkyl, alkenyl, or alkynyl group in which at least one of the hydrogens in the group has been replaced with a halogen atom.

The term aryl, as used herein, and unless otherwise specified, refers to phenyl, biphenyl, or naphthyl, and preferably phenyl. The aryl group can be optionally substituted with one or more moieties selected from the group consisting of alkyl, hydroxyl, amino, alkylamino, arylamino, alkoxy, aryloxy, nitro, cyano, sulfonic acid, sulfate, phosphonic acid, phosphate, or phosphonate, $CO_2H$, or its pharmaceutically acceptable salt, $CO_2$(alkyl, aryl, alkaryl or aralkyl), or glucamine, either unprotected, or protected as necessary, as known to those skilled in the art, for example, as taught in Greene, et al., "Protective Groups in Organic Synthesis," John Wiley and Sons, Second Edition, 1991.

The term alkoxy, as used herein, and unless otherwise specified, refers to a moiety of the structure —O-alkyl.

The term acyl, as used herein, refers to a group of the formula C(O)R', wherein R' is an alkyl, aryl, alkaryl or aralkyl group.

The term heteroaryl or heteroaromatic, as used herein, refers to an aromatic moiety that includes at least one sulfur, oxygen, or nitrogen in the aromatic ring. Nonlimiting examples are phenazine, phenothiazine, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, morpholinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkyipyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heteroaromatic can be partially or totally hydrogenated as desired. As a nonlimiting example, dihydropyridine can be used in place of pyridine. Functional oxygen and nitrogen groups on the heterocyclic base can be protected as necessary or desired during the reaction sequence. Suitable protecting groups are well known to those skilled in the art, and include trimethylsilyl, dimethylhexylsilyl, t-butyldimethylsilyl, and t-butyldiphenylsilyl, tritylmethyl, alkyl groups, acyl groups such as acetyl and propionyl, methylsulfonyl, and p-toluylsulfonyl.

The term hydroxyalkyl, as used herein, refers to a $C_1$ to $C_6$ alkyl group in which at least one of the hydrogens attached to any of the carbon atoms is replaced with a hydroxy group.

The term thiol antioxidant refers to a sulfur containing compound that retards oxidation.

The term pharmaceutically acceptable derivative refers to a derivative of the active compound that upon administration to the recipient, is capable of providing directly or indirectly, the parent compound, or that exhibits activity itself.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "physiologically cleavable leaving group" refers to a moiety that can be cleaved in vivo from the molecule to which it is attached, and includes but is not limited to an organic or inorganic anion, a pharmaceutically acceptable cation, acyl (including but not limited to (alkyl)C(O), including acetyl, propionyl, and butyryl), alkyl, phosphate, sulfate and sulfonate.

The term "enantiomerically enriched composition or compound" refers to a composition or compound that includes at least 95%, and preferably at least 97, 98, 99, or 100% by weight of a single enantiomer of the compound.

The term amino acid includes synthetic and naturally occurring amino acids, including but not limited to, for example, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, gluatoyl, lysinyl, argininyl, and histidinyl.

A "linking moiety" as used herein, is any divalent group that links two chemical residues, including but not limited to alkyl, alkenyl, alkynyl, aryl, polyalkyleneoxy (for example —$[(CH_2)_nO—]_n$), —$C_{1-6}$alkoxy-$C_{1-10}$alkyl-, —$C_1$-alkylthio-$C_{1-10}$ alkyl-, —$NR^3$—, and —$(CHOH)_nCH_2OH$, wherein n is independently 0, 1, 2, 3, 4, 5, or 6.

II. Identification of Oxidized and Unoxidized Polyunsaturated Fatty Acids as Direct Mediators of VCAM-1 Expression To establish whether a PUFA or oxidized PUFA acts as a direct immunomodulator of endothelial cell gene expression, early passaged human aortic endothelial cells (HAEC) were cultured for eight hours in media and serum and exposed to saturated (stearic), monounsaturated (oleic), and polyunsaturated (linoleic and arachidonic) fatty acids; as well as with the fatty acid hydroperoxides of linoleic (13-HPODE) or arachidonic (15-HPETE) acids. HAEC were also alternatively exposed to the cytokine tumor necrosis factor-α.

HAEC were exposed to linoleic acid or 13-HPODE for varying times up to 48 hours and then assayed for cell surface VCAM-1 expression by ELISA assay. The results were compared to HAEC exposed to the cytokine TNF-α (100 U/ml) for the same time periods. VCAM-1 expression in HAEC incubated with either linoleic acid or 13-HPODE is transiently induced. The expression peaks at approximately 8–9 hours with significant expression at 24 hours and then decreases by 48 hours. The kinetics of VCAM-1 induction by both linoleic acid and 13-HPODE mirror that of TNF-α, and thus the mechanisms by which polyunsaturated fatty acids induce VCAM-1 thus appear to be similar to that of TNF-α.

Dose-response studies of linoleic acid and 13-HPODE on VCAM-1 gene expression at 8 hours were also conducted. It was observed that 7.5 μM is the lowest peak dose by which linoleic acid and 13-HPODE induces significant VCAM-1 gene expression.

It was then explored whether short term incubation of endothelial cells with polyunsaturated fatty acids induces ICAM-1 and E-selectin expression as well. It was determined that the polyunsaturated fatty acids linoleic and arachidonic acids induced cell-surface gene expression to approximately 59% of TNF-induced gene expression of VCAM-1. Strikingly, neither ICAM-1 nor E-selectin were induced by these fatty acids. Conversely, the saturated fatty acid stearic acid and the monounsaturated fatty acid oleic acid did not induce the expression of VCAM-1, ICAM-1, or E-selectin. VCAM-1 gene expression was also observed by incubation of HAEC with the oxidized metabolites of linoleic acid (13-HPODE) and arachidonic acid (15-HPETE).

To investigate whether oxidative stress in endothelial cells provided by polyunsaturated fatty acids and their oxidized metabolites induces VCAM-1 through a redox-sensitive mechanism, HAEC were pretreated with the antioxidant pyrrolidine dithiocarbamate (PDTC, 50 $\mu$M) for 30 minutes and then the cells were independently incubated with linoleic acid, arachidonic acid, 13-HPODE, and 15-HPETE (all 7.5 $\mu$M) for 8 hours. It was determined that PDTC suppressed the gene expression of VCAM-1 induced by the polyunsaturated fatty acids and their oxidized counterparts. This indicates that the induction is mediated by a oxidized signal molecule, and that the induction is prevented when the oxidation of the molecule is blocked (i.e., the oxidation does not occur), reversed (i.e., the signal molecule is reduced), or its interaction with a target protein prevented, perhaps through a redox complex.

To determine whether the selective induction of VCAM-1 by PUFAs and their oxidized metabolites is observed at the mRNA level, HAEC were incubated with linoleic acid or 13-HPODE. Linoleic acid and 13-HPODE induced VCAM-1 mRNA accumulation that was similar to levels induced by TNF-$\alpha$. In contrast, there was no induction of ICAM-1 or E-selectin gene expression at the mRNA level in HAEC incubated with linoleic acid or 13-HPODE. The findings mimic those found at the cell-surface level. These results indicate that pretranslational regulatory mechanisms mediate induction of VCAM-1 gene expression by polyunsaturated fatty acids and their oxidative metabolites.

It was also desired to determine whether polyunsaturated fatty acids work as a primary signal or operate through a regulatory protein involving the cytokine IL-4,in inducing VCAM-1 gene expression. To investigate whether newly synthesized proteins such as IL-4 are involved in the synthesis and gene expression of VCAM-1 induced by PUFAs such as linoleic acid, HAEC were incubated with 13-HPODE (7.5 $\mu$M) and exposed to the protein synthesis inhibitor, cycloheximide. There was no inhibition of mRNA accumulation of VCAM-1 by cycloheximide in HAEC incubated with 13-HPODE. The production of IL-4 by HAEC incubated with linoleic or arachidonic acids and their oxidative metabolites, as determined by ELISA was also measured. There was no increase in IL-4 output by HAEC incubated with these PUFAs or their oxidized metabolites.

Previous investigations have demonstrated through deletion and heterologous promoter studies that cytokines and non-cytokines activate VCAM-1 gene expression in endothelial cells at least in part transcriptionally through two NF-kB-like DNA binding elements. It has also been demonstrated that PDTC inhibits VCAM-1 gene expression through a redox-sensitive NF-kB like factor. To determine whether polyunsaturated fatty acids induce transcriptional activation of the human VCAM-1 promoter via a similar mechanism, the chimeric reporter gene p288 VCAM-CAT, containing coordinates −288 to +22 of the human VCAM-1 promoter, was transiently transfected into HAEC. The addition of linoleic acid (7.5 $\mu$M) induced VCAM-1 promoter. The addition of linoleic acid (7.5 $\mu$M) induced VCAM-I promoter activity that was over two fold that of the control and approximately 60% of the maximum signal induced by TNF-$\alpha$. Similar results were obtained with the minimal cytokine-inducible promoter of the VCAM-1 gene (p85 VCAM-CAT), containing the −77 and −63 bp NF-kB-like sites. Neither linoleic acid nor TNF-$\alpha$ had any effect on activity using a constitutively expressed pSV$_2$ CAT construct. PDTC inhibited the transcriptional activation of both VCAM-1 promoter constructs induced by linoleic acid. The data indicate that analogous to TNF-$\alpha$, polyunsaturated fatty acids such as linoleic acid induce the transcriptional activation of VCAM-1 through an NF-kB-like redox-sensitive mechanism.

Figure 7A:
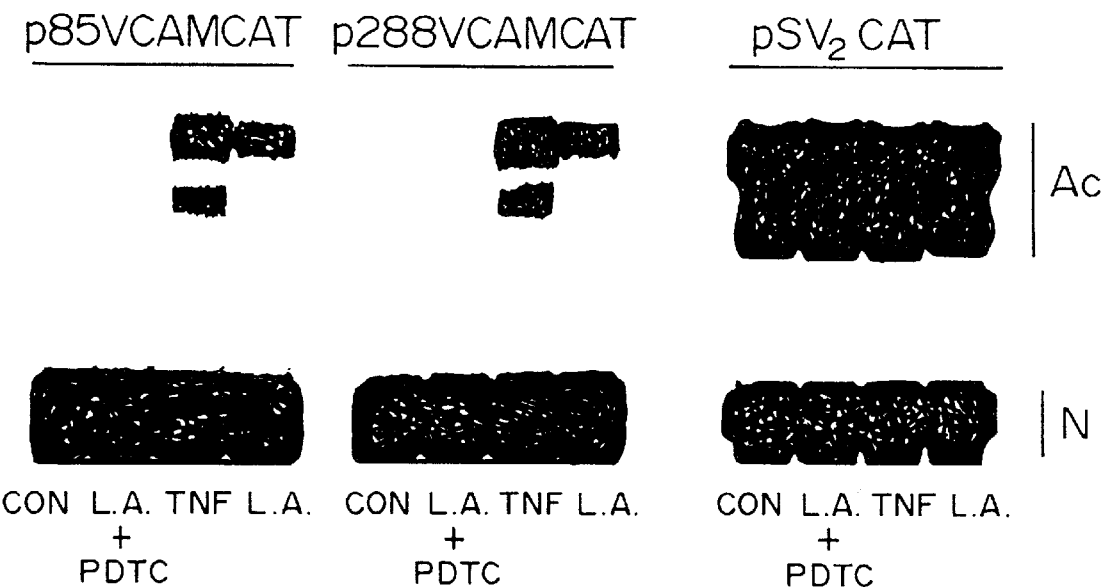
FIG. 7 is an illustration of an autoradiogram that indicates that linoleic acid induces transcriptional activation of the VCAM-1 promoter by a redox-sensitive NF-kB like factor. HAEC were split at the ratio to give approximately 60% confluence in 100-mm tissue culture plates. HAEC were transfected with either 30 $\mu$g of p288 VCAMCAT, p85 VCAMCAT, or pSV$_2$CAT plasmid by the calcium phosphate coprecipitation technique using standard techniques. After a 24-hour recovery period, HAEC were pretreated or not with 50 $\mu$M PDTC and after 30 minutes exposed to linoleic acid (7.5 $\mu$M) or TNF-α (100 U/ml) directly added to the plates. After 18 hours, cell extracts were prepared by rapid freeze-thaw in 0.25M Tris, pH 8.0. The protein of each cell extract was assayed for chloramphenicol acetyl transferase (CAT) activity, as previously described. (Ausubel, 1989) (Ac, acetylated; N, nonacetylated chloramphenicol).
Figure 7B:
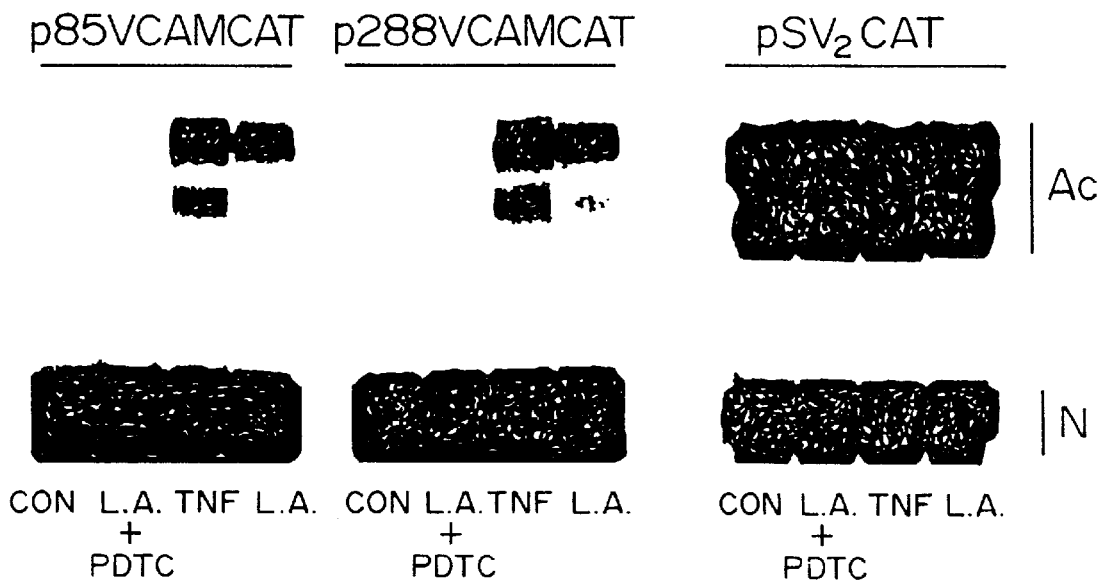

To determine whether polyunsaturated fatty acids and their oxidative metabolites regulate VCAM-1 promoter activity through an NF-kB-like transcriptional regulatory factor, nuclear extracts from HAEC were assayed for DNA binding activity to a double-stranded oligonucleotide containing the VCAM-1 NF-kB-like promoter elements located at positions −77 and −63. As shown in FIG. 7, two bands A and C, representing NF-kB-like activity were induced in response to a three hour exposure to linoleic acid (7.5 $\mu$M). Similar findings were observed on exposure to the cytokine TNF-$\alpha$ (100 U/ml). A weak band B was observed in control (untreated) cells. No induction of NF-kB-like binding was observed with the monounsaturated fatty acid oleic acid. Pretreatment of the cells for thirty minutes with PDTC inhibited the A and C complex DNA binding activity after linoleic acid activation. These findings are similar to previously reported findings that PDTC blocks the activation of VCAM-1 gene expression in HUVEC by inhibiting the activation of these NF KB-like DNA binding proteins.

EXAMPLE 1

Figure 2:
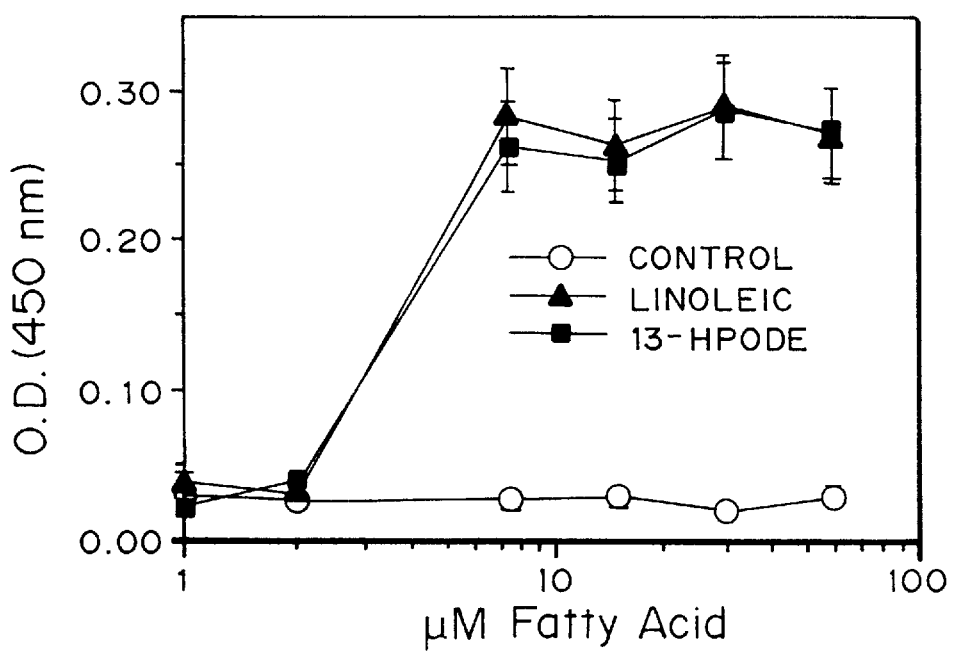
FIG. 2 is a graph of the cell-surface expression (O.D. 450 nm) of VCAM-1 in human aortic endothelial cells on exposure to linoleic acid (closed triangle) and linoleyl hydroperoxide (13-HPODE, closed square) as a function of the concentration of fatty acid ($\mu$M).

Effect of Oxidized and Unoxidized Polyunsaturated Patty Acids on the Kinetics of the Activation of VCAM-L Gene Expression Human aortic endothelial cells (HAEC) were plated in 96 well plates and incubated with linoleic acid (7.5 $\mu$M), 13-HPODE (7.5 $\mu$M), or TNF-$\alpha$ (100 U/ml) at five different time points up to 48 hours. HAEC, obtained from Clonetics (Boston, Mass.), were cultured in Medium 199 supplemented with 20% fetal bovine serum (FBS), 16 U/ml heparin, 10 U/ml epidermal growth factor, 50 $\mu$g/ml endothelial cell growth supplement, 2 mM L-glutamine, 100 U/ml penicillin, and 100 $\mu$g/ml streptomycin. One day before the experiment, cells were placed in a medium containing 4% FBS. Confluent HAEC were incubated for up to 48 hours with TNF-$\alpha$ (100 U/ml), or stearic, oleic, linoleic, linolenic, or arachidonic acids (7.5 $\mu$M). Similar studies were performed with differing doses of linoleic acid or 13-HPODE for an 8 hour period (1–60 $\mu$M) (FIG. 2). Quantitation was performed by determination of calorimetric conversion at 450 nm of TMB. Studies were performed in triplicate (n=4 for each experimental value). *-value differs (p<0.05) from Control.

As shown in FIG. 1, both linoleic acid and 13-HPODE induced the expression of VCAM-1. At ten hours after exposure, the amount of cell surface VCAM-1 induced by linoleic acid and 13-HPODE was greater than half that induced by the cytokine TNF-$\alpha$.

As shown in FIG. 2, the induction of VCAM-1 by linoleic acid and 13-HPODE is concentration sensitive. At a concentration of between 2 and 10 $\mu$M of these compounds, there is a sharp increase in the amount of induced cell surface VCAM-1, which then remains approximately constant up to a concentration of at least 100 $\mu$M. It should be observed that the PUFA concentration indicated in FIG. 2 is in addition to that found endogenously in HAEC.

EXAMPLE 2

Polyunsaturated Fatty Acids Induce Gene Expression of VCAM-1 but not ICAM-1 or 1-selectin The cell surface expression of VCAM-1, ICAM-1, and E-selectin was measured in HAEC by ELISA. HAEC, obtained from Clonetics (California), were cultured in Medium 199 supplemented with 20% fetal bovine serum (FBS), 16 U/ml heparin, 10 U/ml epidermal growth factor, 50 μg/ml endothelial cell growth supplement, 2 mM L-glutamine, 100 U/ml penicillin, and 100 μg/ml streptomycin. One day before the experiment, cells were placed in a medium containing 4% FBS. Confluent HAEC were incubated or not for 8 hours with TNF-α (100 U/ml), or stearic, oleic, linoleic, linolenic, or arachidonic acids (7.5 μM). Cell-surface expression of A) VCAM-1, B) ICAM-1, and C) E-selectin was determined by primary binding with VCAM-1 specific, ICAM-1 specific, and E-selectin specific mouse antibodies followed by secondary binding with a horseradish peroxidase-tagged goat anti-mouse (IgG). Quantitation was performed by determination of calorimetric conversion at 450 mm of TMB. Studies were performed in triplicate (n=4 for each experimental value). *-value differs (p<0.05) from Control.

Figure 3A:
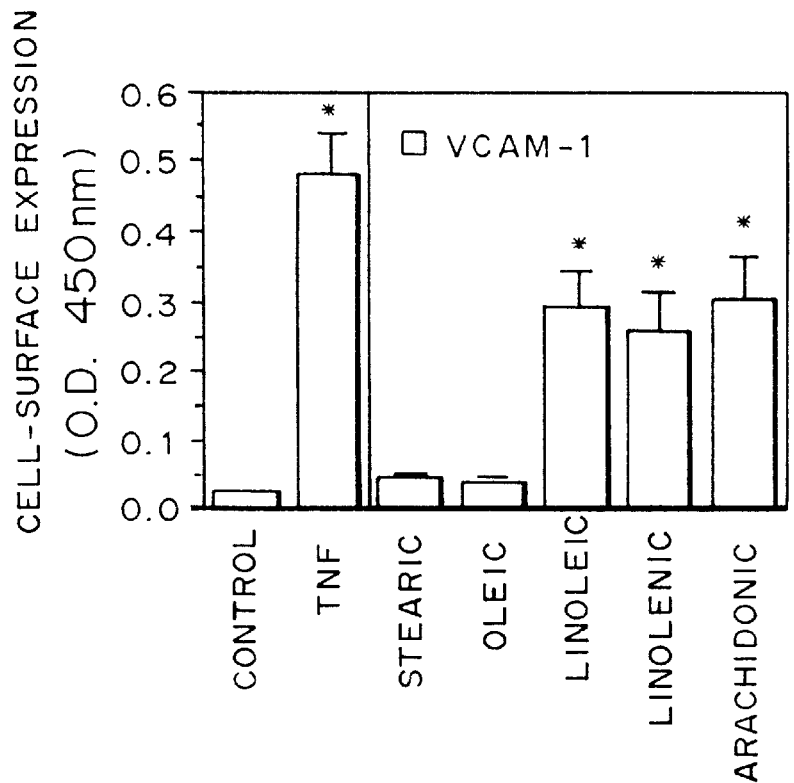
FIG. 3 is a bar chart graph of the cell-surface expression (O.D. 450 nm) of VCAM-1, ICAM-1 and E-selectin in human aortic endothelial cells on exposure to the cytokine TNF-α, stearic acid, oleic acid, linoleic acid, linolenic acid, and arachidonic acid.
Figure 3B:
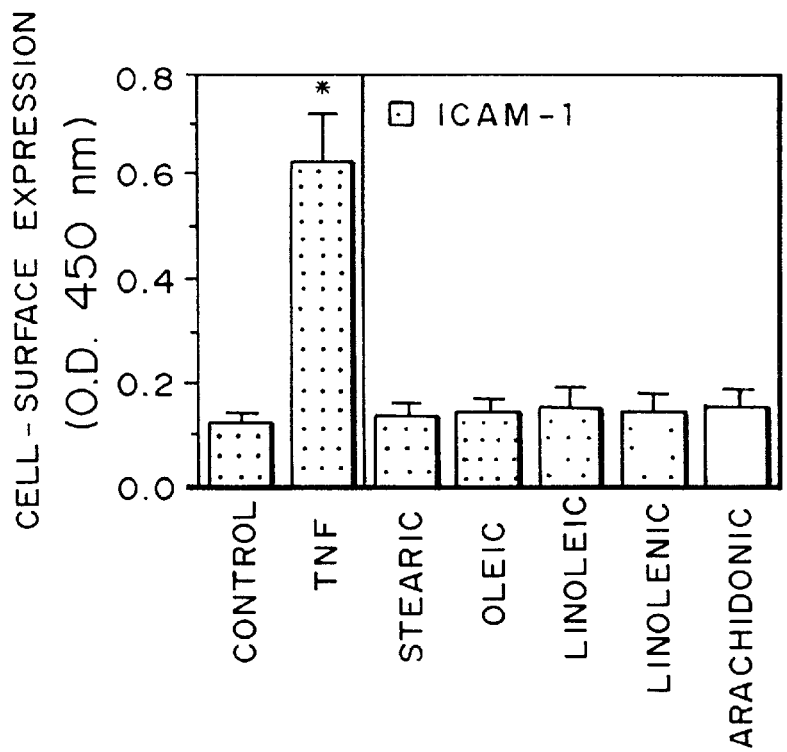
Figure 3C:
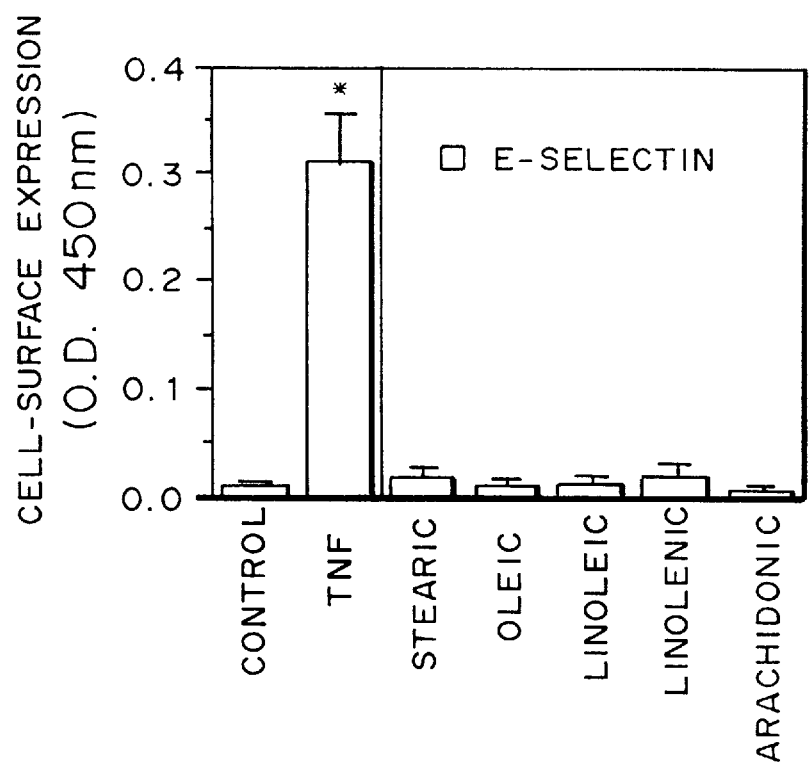

As shown in FIG. 3, linoleic acid, linolenic acid, and arachidonic acid significantly induced the expression of VCAM-1, but did not induce the cell-surface expression of ICAM-1 or E-selectin. Neither stearic acid nor oleic acid induced the expression of VCAM-1, ICAM-1, or E-selectin. TNF-α strongly induced the expression of all three cell-surface molecules.

EXAMPLE 3

The Antioxidant PDTC Suppresses VCAM-1 Induction by Polyunsaturated Patty Acids and their Oxidative Metabolites Confluent HAEC were pretreated in the presence or absence of PDTC (sodium pyrrolidine dithiocarbamate, 50 μM) for thirty minutes. The cells were then incubated for eight hours with TNF-α (100 U/ml), linoleic or arachidonic acid (7.5 μM), or the fatty acid hydroperoxides 13-HPODE (7.5 μM) or 15-HPETE (7.5 μM). The cell surface expression of VCAM-1 was measured in HAEC by ELISA, as described in Example 1. Studies were performed in triplicate (n =4 for each experimental value). *-value differs (p<0.05) from control.

Figure 4:
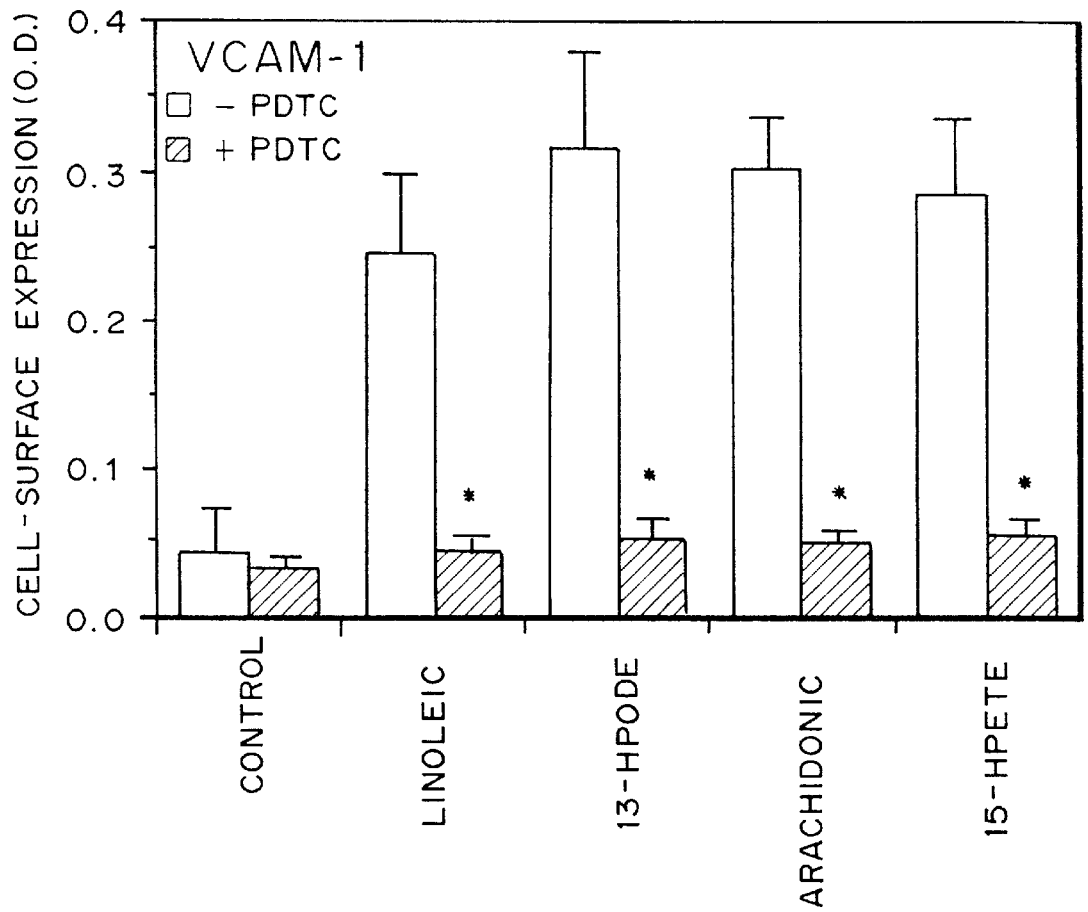
FIG. 4 is a bar chart graph of the cell-surface expression (O.D. 450 nm) of VCAM-1 in human aortic endothelial cells on exposure to linoleic acid, 13-HPODE, arachidonic acid, and arachidonic acid hydroperoxide (15-HPETE), with (solid black) or without (hatched lines) the antioxidant pyrrolidine dithiocarbamate.

As indicated in FIG. 4, PDTC suppresses the induction of VCAM-1 by linoleic acid, 13-HPODE, arachidonic acid and 15-HPETE.

EXAMPLE 4

Acute Induction of VCAM-1 mRNA by Linoleic Acid and 13-HPODE

HAEC were exposed to linoleic acid (7.5 μM) or 13-HPODE (7.5 μM). Total RNA was isolated and 20 μg size-fractionated by denaturing 1.0% agarose-formaldehyde gel electrophoresis, transferred to nitrocellulose, and hybridized to either $^{32}$P-labeled human A) VCAM-1 specific or B) β-actin specific CDNA and visualized by autoradiography. After washes, filters were exposed to X-ray film at −70° C. with one intensifying screen for 24 hours. Identification of lanes: 1) control; 2) linoleic acid (acute, 8-hour exposure); 3) linoleic (48-hour exposure); 4) 13-HPODE (acute, 8-hour exposure); and 5) TNF-α (100 U/ml, 4-hour exposure).

Figure 5:
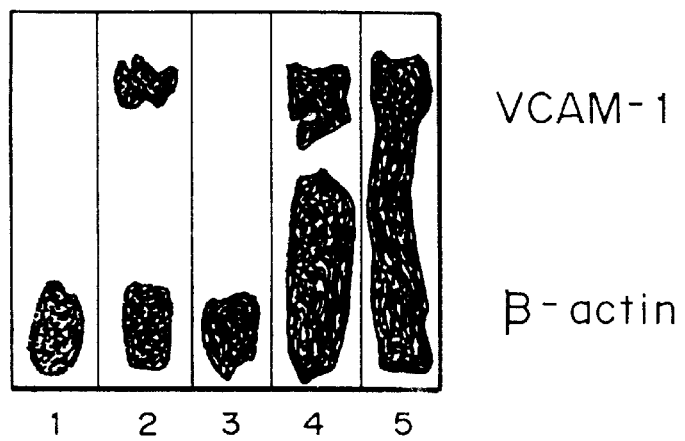
FIG. 5 is an illustration of an autoradiogram indicating the acute induction of VCAM-1 mRNA by linoleic acid and 13-HPODE. HAEC were exposed or not to linoleic acid (7.5 $\mu$M), 13-HPODE (7.5 $\mu$M) or TNF-α (100 U/ml). Total RNA was isolated and 20 $\mu$g was size-fractionated by denaturing 1.0% agarose-formaldehyde gel electrophoresis, transferred to nitrocellulose, and hybridized to either $^{32}$P-labeled human A) VCAM-1 specific or B) β-actin specific cDNA. After washing, the filters were exposed to X-ray film at −70° C. with one intensifying screen for 24 hours. Identification of lanes: 1) control; 2) linoleic acid (acute, 8-hour exposure); 3) linoleic acid (48-hour exposure); 4) 13-HPODE (acute, 8-hour exposure); and 5) TNF-α (100 U/ml, 4-hour exposure).
Figure 6A:
FIG. 6 is an illustration of an autoradiogram that indicates that induction of VCAM-1 mRNA by polyunsaturated fatty acids is independent of cellular protein synthesis. HAEC were exposed to either linoleic (7.5 $\mu$M) or arachidonic (7.5 $\mu$M) acid in the presence or absence of cycloheximide (10 $\mu$g/ml) for a 4-hour period, and then treated as described in FIG. 5.
Figure 6B:
Figure 6C:
Figure 6D:
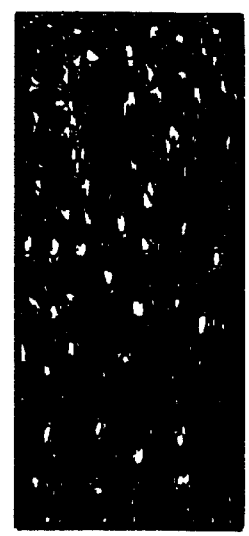

As shown in FIG. 5, both linoleic acid and 13-HPODE induce the production of mRNA for VCAM-1 in eight hours. After 48 hours, linoleic acid no longer induces VCAM-1 mRNA.

EXAMPLE 5

Induction of VCAM-1 mRNA by PUFAs is Independent of Cellular Protein Synthesis

HAEC were exposed to either linoleic or arachidonic acid (7.5 μM) in the presence or absence of cycloheximide (10 μg/ml) for a 4-hour period. Total RNA was isolated and 20 μg was size-fractionated by denaturing 1.0% agarose-formaldehyde gel electrophoresis, transferred to nitrocellulose, and hybridized to A) 32P-labeled human VCAM-1 or B) β-actin specific cDNA and then visualized by autoradiography. After washes, filters were exposed to X-ray film at −70° C. with one intensifying screen for 24 hours.

As indicated in FIG. 6, the induction of VCAM-1 by linoleic and arachidonic acids are independent of cellular protein synthesis.

EXAMPLE 6

Linoleic acid induces transcriptional activation of the VCAM-1 promoter by a redox-sensitive NF-kB like factor HAEC were split at the ratio to give approximately 60% confluence in 100-mm tissue culture plates. HAEC were transfected with either 30 μg of p288 VCAMCAT, p85 VCAMCAT, or pSV$_2$CAT plasmid by the calcium phosphate coprecipitation technique using standard techniques. After a 24-hour recovery period, HAEC were pretreated with 50 μM PDTC and after 30 minutes exposed to linoleic acid (7.5 μM) or TNF-α (100 U/ml) directly added to the plates. After 18 hours, cell extracts were prepared by rapid freeze-thaw in 0.25M Tris, pH 8.0. Protein of each cell extract was assayed for chloramphenicol acetyl transferase (CAT) activity (Ac, acetylated; N, nonacetylated chloramphenicol).

FIG. 7 illustrates the results of this experiment. Linoleic acid induces transcriptional activation of the VCAM-1 promoter by a redox-sensitive NF-kB like factor. These results are similar to those observed by the activation of VCAM-1 promotor by cytokines such as TNF-α. This suggests that PUFAs act through an oxidized intermediate that also mediates the cytokine activation of VCAM-1.

EXAMPLE 7

Polyunsaturated Fatty Acid Activate NP-kB-like DNA Binding Activities that are Blocked by the Antioxidant PDTC Confluent HAEC in media containing 4% FBS (as described in Example 1) were pretreated with PDTC (50 μM) for 30 minutes and then exposed for 3 hours to linoleic acid or oleic acid (7.5 μM), or TNF-α (100 U/ml). Five micrograms of nuclear extract was incubated with a double-stranded $^{32}$P-labeled wtVCAM, size fractionated on 4% native acrylamide gels, and exposed to autoradiography film at −70° C. for 18 hours. Two bands A and C, representing NF-kB like binding activity are designated. A weak band B was observed in control (untreated) cells.

Figure 8A:
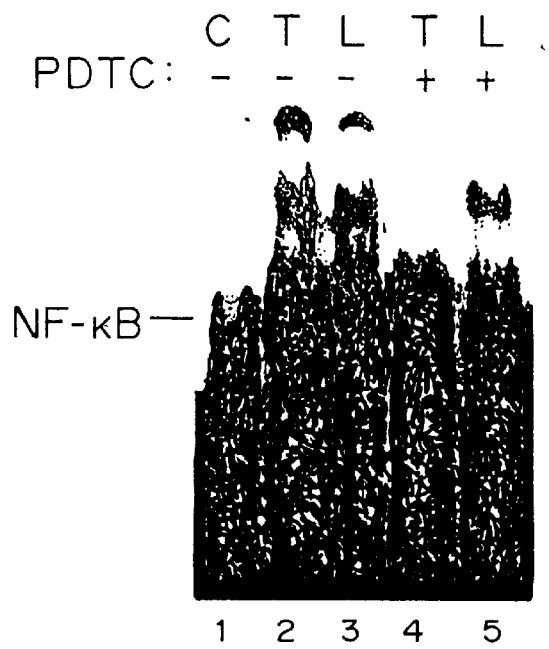
FIG. 8 is an illustration of an acrylamide gel slab that indicates that polyunsaturated fatty acids activate NF-kB-like DNA binding activities that are blocked by the antioxidant PDTC. Confluent HAEC in media containing 4% FBS (as described in FIG. 1) were pretreated or not with PDTC (50 $\mu$M) for thirty minutes and then exposed for three hours to linoleic acid (7.5 $\mu$M, oleic acid (7.5 $\mu$M), or TNFα (100 U/ml), respectively. Five micrograms of nuclear extract was incubated with a double-stranded $^{32}$P-labeled wtVCAM, size fractionated on 4% native acrylamide gels, and exposed to autoradiography film at −70° C. for 18 hours. Two bands A and C, representing NF-kB like binding activity are designated. A weak band B was observed in control (untreated) cells.
Figure 8B:
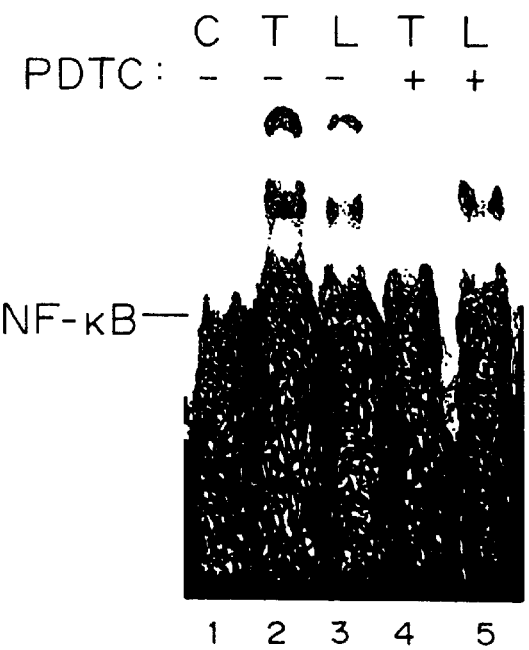

FIG. 8 illustrates that linoleic acid induces NF-kβ binding activity to VCAM-1 promotor in a redox-sensitive manner. This is analogous to cytokine TNF-α and suggests a similar mechanism of action. TNF-α probably induces VCAM-1 through a mechanism that is mediated by an ox-PUFA.

EXAMPLE 8

Figure 9A:
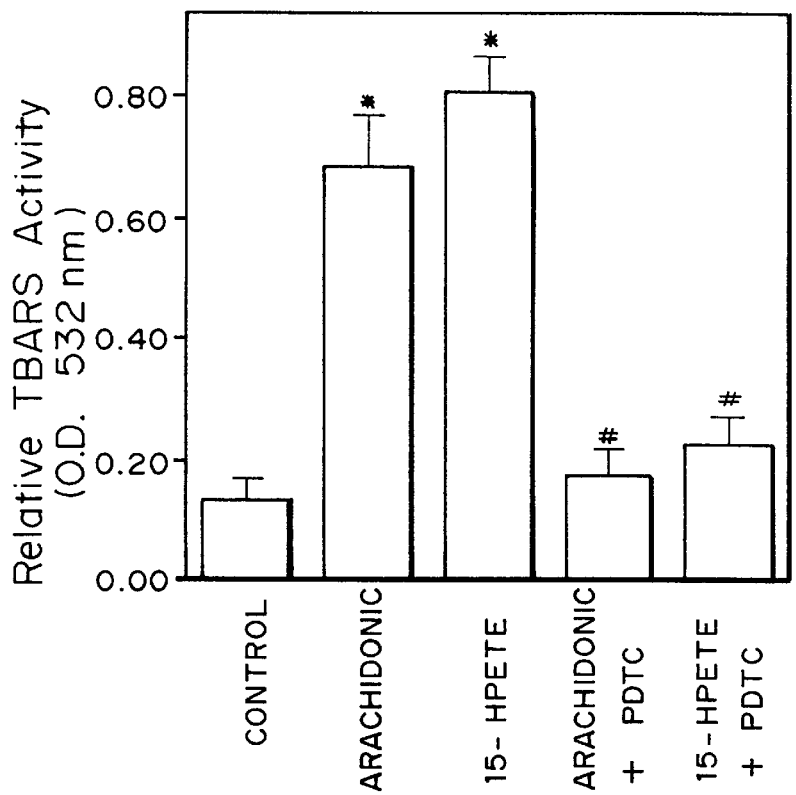
FIGS. 9A and 9B are bar chart graphs of the relative thiabarbituric acid reactive substances (O.D. 532 nm) of arachidonic acid and 15-HPETE in the presence or absence of PDTC. The thiobarbituric acid reactivity assay (TBARS) measures the oxidation ability of a material in a cell-free, media-free environment.
Figure 9B:
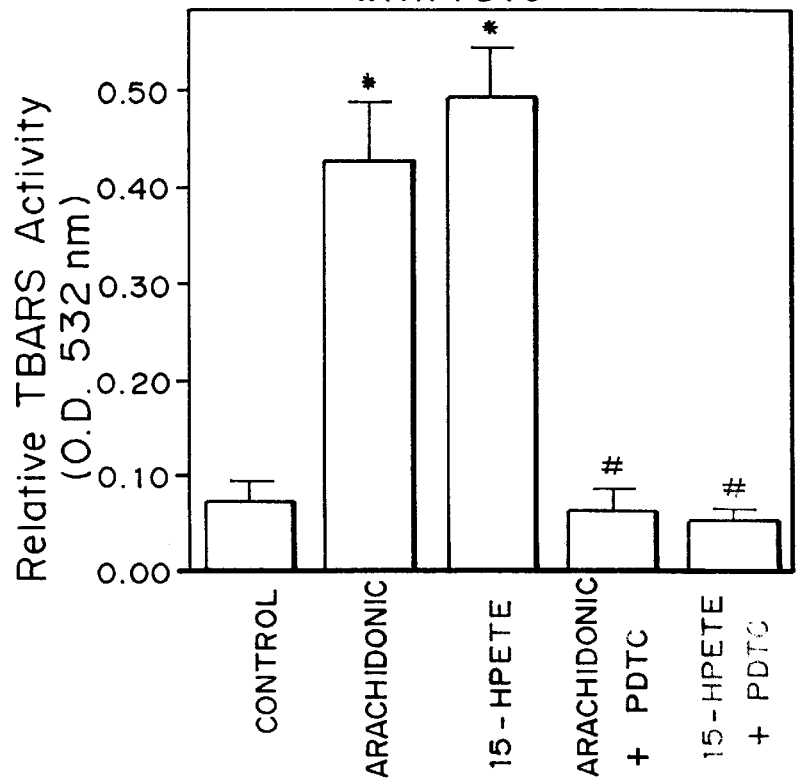

Oxidation in a Cell-Free, Media-Free Setup, by Both Unoxidized and Oxidized (15-HEPTE) Arachidonic Acid FIGS. 9A and 9B are bar chart graphs of the relative thiabarbituric acid reactive substances (O.D. 532 nm) of arachidonic acid and 15-HPETE in the presence or absence of PDTC. The thiobarbituric acid reactivity assay (TBARS) measures the oxidation ability of a material in a cell-free, media-free environment. As indicated in the Figures, both arachidonic acid and 15-HPETE showed significant TBARS activity that was inhibited by PDTC.

III. Method for the Treatment of VCAM-1 Mediated Disorders

The discovery that polyunsaturated fatty acids and their oxidized metabolites are selective, redox-sensitive immunomodulators provides a basis for the therapy of disorders that are mediated by VCAM-1 or by redox-sensitive genes.

A method for the treatment of atherosclerosis, post-angioplasty restenosis, coronary artery diseases, angina, and other cardiovascular diseases, as well as noncardiovascular inflammatory diseases that are mediated by VCAM-1 is provided that includes the removal, decrease in the concentration of, or prevention of the formation of oxidized polyunsaturated fatty acids, including but not limited to oxidized linoleic, linolenic, and arachidonic acids. In an alternative embodiment, a method for the treatment of these diseases is provided that includes the prevention of the interaction of a PUFA or ox-PUFA with a protein or peptide that mediates VCAM-1 expression.

Inhibition of the expression of VCAM-1 can be accomplished in a number of ways, including through the administration of an antioxidant that prevent the oxidation of a polyunsaturated fatty acid, by in vivo modification of the metabolism of PUFAs into ox-PUFAs, as described in more detail below.

1. Administration of Antioxidants

Any compound that reduces an ox-PUFA or which inhibits the oxidation of PUFA, and which is relatively nontoxic and bioavailable or which can be modified to render it bioavailable, can be used in this therapy. One of ordinary skill in the art can easily determine whether a compound reduces an ox-PUFA or inhibits the oxidation of PUFA using standard techniques.

Dithiocarboxylate Antioxidants

It has been discovered that dithiocarboxylates are useful in the treatment of atherosclerosis and other cardiovascular and inflammatory diseases. Dithiocarboxylates, including dithiocarbamates, can be used to block the ability of cells, including endothelial cells, to express VCAM-1 or to suppress the expression of a redox-sensitive gene or activate a gene that is suppressed through a redox-sensitive pathway.

At least one of the compounds, pyrrolidine dithiocarbamate (PDTC), inhibits VCAM-1 gene expression at a concentration of less than 1.0 micromolar. This compounds also exhibits preferential toxicity to proliferating or abnormally dividing vascular smooth muscle cells. Another dithiocarbamate, sodium N-methyl-N-carboxymethyl-N-carbodithioate, also inhibits the expression of VCAM-1, without significant effect on ICAM-1, but does not exhibit preferential toxicity to abnormally dividing vascular smooth muscle cells. Another dithiocarbamate, sodium N-methyl-N-carboxymethyl-N-carbodithioate, also inhibits the expression of VCAM-1, without significant effect on ICAM-1, but does not exhibit preferential toxicity to abnormally dividing vascular smooth muscle cells.

It has been discovered that pyrrolidine dithiocarbamate does not significantly block ELAM-1 or ICAM-1 expression, and therefore treatment with this compound does not adversely affect aspects of the inflammatory response mediated by ELAN-1 or ICAM-1. Thus, a generalized immunosuppression is avoided. This may avoid systemic complications from generalized inhibition of adhesion molecules in the many other cell types known to express them. Other pharmaceutically acceptable salts of PDTC are also effective agents for the treatment of cardiovascular and inflammatory disorders.

Dithiocarbamates are transition metal chelators clinically used for heavy metal intoxication. Baselt, R. C., F. W. J. Sunderman, et al. (1977), "Comparisons of antidotal efficacy of sodium diethyldithiocarbamate, D-penicillamine and triethylenetetramine upon acute toxicity of nickel carbonyl in rats." Res Commun Chem Pathol Pharmacol 18(4): 677–88; Menne, T. and K. Kaaber (1978), "Treatment of pompholyx due to nickel allergy with chelating agents." Contact Dermatitis 4(5): 289–90; Sunderman, F. W. (1978), "Clinical response to therapeutic agents in poisoning from mercury vapor" Ann Clin Lab Sci 8(4): 259–69; Sunderman, F. W. (1979), "Efficacy of sodium diethyldithiocarbamate (dithiocarb) in acute nickel carbonyl poisoning." Ann Clin Lab Sci 9(1): 1–10; Gale, G. R., A. B. Smith, et al. (1981), "Diethyldithiocarbamate in treatment of acute cadmium poisoning." Ann Clin Lab Sci 11(6): 476–83; Jones, M. M. and M. G. Cherian (1990), "The search for chelate antagonists for chronic cadmium intoxication." Toxicology 62(1): 1–25; Jones, S. G., M. A. Basinger, et al. (1982), "A comparison of diethyldithiocarbamate and EDTA as antidotes for acute cadmium intoxication." Res Commun Chem Pathol Pharmacol 38(2): 271–8; Pages, A., J. S. Casas, et al. (1985), "Dithiocarbamates in heavy metal poisoning: complexes of N,N-di(1-hydroxyethyl)dithiocarbamate with Zn(II), Cd(II), Hg(II), CH3Hg(II), and $C_6H5Hg(II)$".: J. Inorg Biochem 25(1): 35–42; Tandon, S. K., N. S. Hashmi, et al. (1990), "The lead-chelating effects of substituted dithiocarbamates." Biomed Environ Sci 3(3): 299–305.

Dithiocarbamates have also been used adjunctively in cis-platinum chemotherapy to prevent renal toxicity. Hacker, M. P., W. B. Ershler, et al. (1982). "Effect of disulfiram (tetraethylthiuram disulfide) and diethyldithiocarbamate on the bladder toxicity and antitumor activity of cyclophosphamide in mice." Cancer Res 42(11): 4490–4. Bodenner, 1986 #733; Saran, M. and Bors, W. (1990). "Radical reactions in vivo—an overview." Radiat. Environ. Biophys. 29(4) :249–62.

A dithiocarbamate currently used in the treatment of alcohol abuse is disulfiram, a dimer of diethyldithiocarbamate. Disulfuram inhibits hepatic aldehyde dehydrogenase. Inoue, K., and Fukunaga, et al., (1982). "Effect of disulfiram and its reduced metabolite, diethyldithiocarbamate on aldehyde dehydrogenase of human erythrocytes." Life Sci 30(5): 419–24.

It has been reported that dithocarbamates inhibit HIV virus replication, and also enhance the maturation of specific T cell subpopulations. This has led to clinical trials of diethyldithiocarbamate in AIDs patient populations. Reisinger, E., et al., (1990). "Inhibition of HIV progression by dithiocarb." Lancet 335: 679.

Dithiocarboxylates are compounds of the structure A-SC (S)-B, which are-members of the general class of compounds known as thiol antioxidants, and are alternatively referred to as carbodithiols or carbodithiolates. It appears that the —SC(S)— moiety is essential for therapeutic activity, and that A and B can be any group that does not adversely affect the efficacy or toxicity of the compound.

In an alternative embodiment, one or both of the sulfur atoms in the dithiocarbamate is replaced with a selenium atom. The substitution of sulfur for selenium may decrease the toxicity of the molecule in certain cases, and may thus be better tolerated by the patient.

A and B can be selected by one of ordinary skill in the art to impart desired characteristics to the compound, including size, charge, toxicity, and degree of stability, (including stability in an acidic environment such as the stomach, or basic environment such as the intestinal tract). The selection of A and B will also have an important effect on the tissue-distribution and pharmacokinetics of the compound. In general, for treatment of cardiovascular disease, it is desirable that the compound accumulate, or localize, in the arterial intimal layer containing the vascular endothelial cells. The compounds are preferably eliminated by renal excretion.

An advantage in administering a dithiocarboxylate pharmaceutically is that it does not appear to be cleaved enzymatically in vivo by thioesterases, and thus may exhibit a prolonged halflife in vivo.

In a preferred embodiment, A is hydrogen or a pharmaceutically acceptable cation, including but not limited to sodium, potassium, calcium, magnesium, aluminum, zinc, bismuth, barium, copper, cobalt, nickel, or cadmium; a salt-forming organic acid, typically a carboxylic acid, including but not limited to acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, or polygalacturonic acid; or a cation formed from ammonia or other nitrogenous base, including but not limited to a nitrogenous heterocycle, or a moiety of the formula $NR^4R^5R^6R^7$, wherein $R^4$, $R^5$, $R^6$, and $R^7$ are independently hydrogen, $C_{1-6}$ linear, branched, or (in the case of $C_{4-6}$) cyclic alkyl, hydroxy($C_{1-6}$)alkyl (wherein one or more hydroxyl groups are located on any of the carbon atoms), or aryl, N,N-dibenzylethylene-diamine, D-glucosamine, choline, tetraethylammonium, or ethylenediamine.

In another embodiment, A can be a physiologically cleavable leaving group that can be cleaved in vivo from the molecule to which it is attached, and includes but is not limited acyl (including acetyl, propionyl, and butyryl), alkyl, phosphate, sulfate or sulfonate.

In one embodiment, B is alkyl, alkenyl, alkynyl, alkaryl, aralkyl, haloalkyl, haloalkenyl, haloalkynyl, aryl, alkaryl, hydrogen, $C_{1-6}$ alkoxy-$C_{1-10}$ alkyl, $C_{1-6}$ alkylthio-$C_{1-10}$ alkyl, $NR^2R^3$, —(CHOH)$_n$CH$_2$OH, wherein n is 0, 1, 2, 3, 4, 5, or 6, —(CH$_2$)$_n$CO$_2R^1$, including alkylacetyl, alkylpropionyl, and alkylbutyryl, or hydroxy($C_{1-6}$)alkyl- (wherein one or more hydroxyl groups are located on any of the carbon atoms).

In another embodiment, B is $NR^2R^3$, wherein $R^2$ and $R^3$ are independently alkyl; —(CHOH)$_n$(CH$_2$)$_n$OH, wherein n is 0, 1, 2, 3, 4, 5, or 6; —(CH$_2$)$_n$CO$_2R^1$, —(CH$_2$)$_n$CO$_2R^4$; hydroxy($C_{1-6}$)alkyl-; alkenyl (including but not limited to vinyl, allyl, and CH$_3$CH=CH—C$_2$CH$_2$); alkyl(CO$_2$H), alkenyl(CO$_2$H), alkynyl(CO$_2$H), or aryl, wherein the aryl group can be substituted as described above, notably, for example, with a NO$_2$, CH$_3$, t-butyl, CO$_2$H, halo, or p-OH group; or $R^2$ and $R^3$ can together constitute a bridge such as —(CH$_2$)$_m$—, wherein m is 3, 4, 5, or 6, and wherein $R^4$ is alkyl, aryl, alkaryl, or aralkyl, including acetyl, propionyl, and butyryl.

In yet another embodiment, B can be a heterocyclic or alkylheterocyclic group. The heterocycle can be optionally partially or totally hydrogenated. Nonlimiting examples are those listed above, including phenazine, phenothiazine, pyridine and dihydropyridine.

In still another embodiment, B is the residue of a pharmaceutically-active compound or drug. The term drug, as used herein, refers to any substance used internally or externally as a medicine for the treatment, cure, or prevention of a disease or disorder. Nonlimiting examples are drugs for the treatment or prevention of cardiovascular disease, including antioxidants such as probucol; nicotinic acid; agents that prevent platelets from sticking, such as aspirin; antithrombotic agents such as coumadin; calcium-channel blockers such as varapamil, diltiazem, and nifedipine; angiotensin converting enzyme (ACE) inhibitors such as captopril and enalopril, β-blockers such as propanalol, terbutalol, and labetalol, nonsteroidal antiinflammatories such as ibuprofen, indomethacin, fenoprofen, mefenamic acid, flufenamic acid, sulindac, or corticosteriods. The —C(S)SA group can be directly attached to the drug, or attached through any suitable linking moiety.

In another embodiment, the dithiocarbamate is an amino acid derivative of the structure $AO_2C$—$R^9$—$NR^{10}$—$C(S)$SA, wherein $R_9$ is a divalent B moiety, a linking moiety, or the internal residue of any of the naturally occurring amino acids (for example, CH$_3$CH for alanine, CH$_2$ for glycine, CH(CH$_2$)$_4$NH$_2$ for lysine, etc.), and $R^{10}$ is hydrogen or lower alkyl.

B can also be a polymer to which one or more dithiocarbamate groups are attached, either directly, or through any suitable linking moiety. The dithiocarbamate is preferably released from the polymer under in vivo conditions over a suitable time period to provide a therapeutic benefit. In a preferred embodiment, the polymer itself is also degradable in vivo. The term biodegradable or bioerodible, as used herein, refers to a polymer that dissolves or degrades within a period that is acceptable in the desired application (usually in vivo therapy), usually less than five years, and preferably less than one year, on exposure to a physiological solution of pH 6–8 having a temperature of between 25° and 37° C. In a preferred embodiment, the polymer degrades in a period of between 1 hour and several weeks, according to the application.

A number of degradable polymers are known. Nonlimiting examples are peptides, proteins, nucleoproteins, lipoproteins, glycoproteins, synthetic and natural polypeptides and polyamino acids, including but not limited to polymers and copolymers of lysine, arginine, asparagine, aspartic acid, cysteine, cystine, glutamic acid, glutamine, hydroxylysine, serine, threonine, and tyrosine; polyorthoesters, including poly(α-hydroxy acids), for example, polylactic acid, polyglycolic acid, poly(lactide-co-glycolide), polyanhydrides, albumin or collagen, a polysaccharide containing sugar units such as lactose, and polycaprolactone. The polymer can be a random or block copolymer.

B can also be a group that enhances the water solubility of the dithiocarbamate, for example, -lower alkyl-O—$R^8$, wherein $R^8$ is —PO$_2$(OH)M$^+$ or PO$_3$(M$^+$)$_2$ wherein M$^+$ is a pharmaceutically acceptable cation; —C(O) (C$_2$)$_2$CO$_2^-$M$^+$, or —SO$_3$—M$^+$; -lower alkylcarbonyl-lower alkyl; -carboxy lower alkyl; -lower alkylamino-lower alkyl; N,N-di-substituted amino lower alkyl-, wherein the substituents each independently represent lower alkyl; pyridyl-lower alkyl-; imidazolyl-lower alkyl-; imidazolyl-Y-lower alkyl wherein Y is thio or amino; morpholinyl-lower alkyl; pyrrolidinyl-lower alkyl; thiazolinyl-lower alkyl-; piperidinyl-lower alkyl; morpholinyl-lower hydroxyalkyl; N-pyrryl; piperazinyl-lower alkyl; N-substituted piperazinyl-lower alkyl, wherein the substituent is lower alkyl; triazolyl-lower alkyl; tetrazolyl-lower alkyl; tetrazolylamino-lower alkyl; or thiazolyl-lower alkyl.

In an alternative embodiment, a dimer such as B—C(S)S—SC(S)—B can be administered.

Nonlimiting examples of dithiocarbamates are those of the structure:

1) Aliphatic Substrate

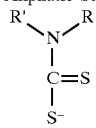

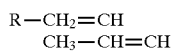

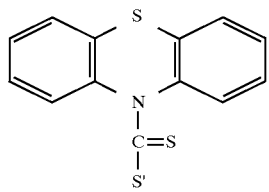

2) Amino acid

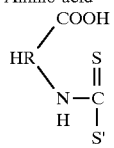

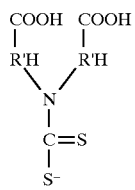

Polyamino acid

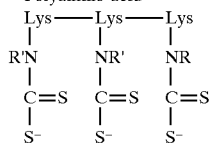

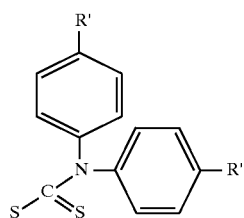

R' Substituents
$NO_2$
$CH_3$ or t-Butyl
COOH
p-OH

R—

R'

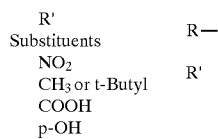

$Na^+$
$Ca^{++}$
$NH_4^+$
Choline$^+$ and quaternary amines
$Mg^{++}$
$Al^{+++}$
$K^+$
$H^+$

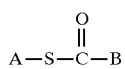

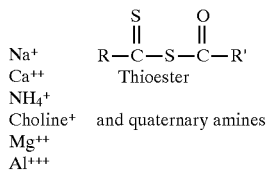

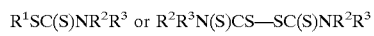

Dihydropyridine, calcium channel blocker nefidipine, and derivatives, substituted and unsubstituted.

Dithiocarboxylates should be chosen for use in treating atherosclerosis and other cardiovascular and inflammatory diseases that have the proper lipophilicity to locate at the affected cite. The compound should not compartmentalize in low turnover regions such as fat-deposits. In a preferred embodiment for treatment of cardiovascular disease, the pharmacokinetics of the compound should not be dramatically affected by congestive heart failure or renal insufficiency.

For topical applications for the treatment of inflammatory skin disorders, the selected compound should be formulated to be absorbed by the skin in a sufficient amount to render a therapeutic effect to the afflicted site.

The dithiocarboxylate must be physiologically acceptable. In general, compounds with a therapeutic index of at least 2, and preferably at least 5 or 10, are acceptable. The therapeutic index is defined as the $EC_{50}/IC_{50}$, wherein $EC_{50}$ is the concentration of compound that inhibits the expression of VCAM-1 by 50% and $IC_{50}$ is the concentration of compound that is toxic to 50% of the target cells. Cellular toxicity can be measured by direct cell counts, trypan blue exclusion, or various metabolic activity studies such as 3H-thymidine incorporation, as known to those skilled in the art. The therapeutic index of PDTC in tissue culture is over 100 as measured by cell toxicity divided by ability to inhibit VCAM-1 expression activated by TNFa, in HUVE cells. Initial studies on the rapidly dividing cell type HT-18 human glioma demonstrate no toxicity at concentrations 100-fold greater than the therapeutic concentration. Disulfiram, an orally administered form of diethyldithiocarbamate, used in the treatment of alcohol abuse, generally elicits no major clinical toxicities when administered appropriately.

There are a few dithiocarbamates that are known to be genotoxic. These compounds do not fall within the scope of the present invention, which is limited to the administration of physiologically acceptable materials. An example of a genotoxic dithiocarbamate is the fungicide zinc dimethyldithiocarbamate. Further, the anticholinesterase properties of certain dithiocarbamates can lead to neurotoxic effects. Miller, D. (1982). Neurotoxicity of the pesticidal carbamates. *Neurobehav. Toxicol. Teratol.* 4(6): 779–87.

The term dithiocarboxylate as used herein specifically includes, but is not limited to, dithiocarbamates of the formulas:

$R^1SC(S)NR^2R^3$ or $R^2R^3N(S)CS-SC(S)NR^2R^3$ wherein $R^1$ is H or a pharmaceutically acceptable cation, including but not limited to sodium, potassium, or $NR^4R^5R^6R^7$, wherein $R^4$, $R^5$, $R^6$, and $R^7$ are independently hydrogen, $C_{1-6}$ linear, branched, or cyclic alkyl, hydroxy ($C_{1-6}$)alkyl (wherein one or more hydroxyl groups are located on any of the carbon atoms), or aryl, and $R^2$ and $R^3$ are independently $C_{1-10}$ linear, branched or cyclic alkyl; —(CHOH)$_n$(CH$_2$)$_n$OH, wherein n is 0, 1, 2, 3, 4, 5, or 6; —(CH$_2$)$_n$CO$_2$R$^1$, —(CH$_2$)(CO$_2$R$^4$; hydroxy(C$_{1-6}$) alkyl-, or $R^2$ and $R^3$ together constitute a bridge such as —(CH$_2$)$_m$— wherein m is 3–6, and wherein $R^4$ is alkyl, aryl, alkaryl, or aralkyl, including acetyl, propionyl, and butyryl.

Figure 15:
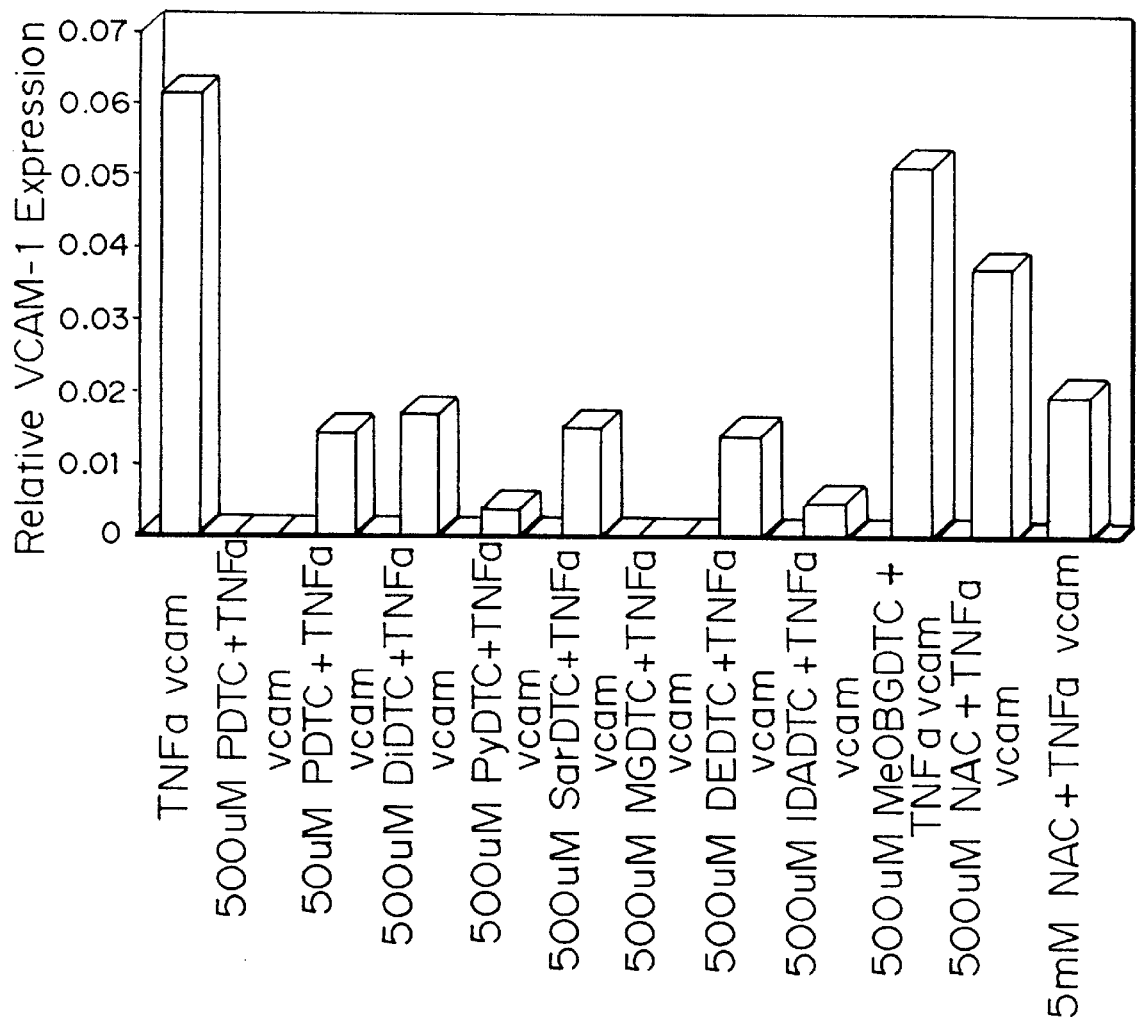
FIG. 15 is a graph of the relative VCAM-1 cell surface expression (O.D. 595 nM) in human umbilical vein endothelial cells, activated by TNF-α, in the presence of the specified amount of antioxidant. (PDTC is sodium N-pyrrolidine dithiocarbamate; DIDTC is sodium N,N-diethyl-N-carbodithioate; SarDTC is sodium N-methyl-N-carboxymethyl-N-carbodithioate; IDADTC is trisodium N,N-di(carboxymethyl)-N-carbodithioate; MGDTC is sodium N-methyl-D-glucamine-N-carbodithioate; MeOB-GDTC is sodium N-(4-methoxybenzyl)-D-glucamine-N-carbodithioate; DEDTC is sodium N,N-diethyl-N-carbodithioate; Di-PDTC is sodium N,N-diisopropyl-N-carbodithioate; NAC is N-acetyl cysteine.)

Specific examples of useful dithiocarbamates, illustrated in FIG. 15, include sodium pyrrolidine-N-carbodithioate, sodium N-methyl-N-carboxymethyl-N-carbodithioate, trisodium N,N-di(carboxymethyl)-N-carbodithioate, sodium N-methyl-D-glucamine-N-carbodithioate, sodium N,N-diethyl-N-carbodithioate (sodium diethyldithiocarbamate), and sodium N,N-diisopropyl-N-carbodithioate.

The active dithiocarboxylates and in particular, dithiocarbamates are either commercially available or can be prepared using known methods.

II. Biological Activity

The ability of dithiocarboxylates to inhibit the expression of VCAM-1 can be measured in a variety of ways, including by the methods set out in detail below in Examples 9 to 15. For convenience, Examples 9–11 and 14–15 describe the evaluation of the biological activity of sodium pyrrolidine-N-carbodithioate (also referred to as PDTC). These examples are not intended to limit the scope of the invention, which specifically includes the use of any of the above-described compounds to treat atherosclerosis, and other types of inflammation and cardiovascular disease mediated by VCAM-1. Any of the compounds described above can be easily substituted for PDTC and evaluated in similar fashion.

Examples 12 and 13 provide comparative data on the ability of a number of dithiocarbamates to inhibit the gene expression of VCAM-1. The examples below establish that the claimed dithiocarbamates specifically block the ability of VCAM-1 to be expressed by vascular endothelial cells in response to many signals known to be active in atherosclerosis and the inflammatory response.

Experimental Procedures

Cell Cultures HUVE cells were isolated from human umbilical veins that were cannulated, perfused with Hanks solution to remove blood, and then incubated with 1% collagenase for 15 minutes at 37° C. After removal of collagenase, cells were cultured in M199 medium supplemented with 20% fetal bovine serum (HyClone), 16 $\mu$g/ml heparin (ESI Pharmaceuticals, Cherry Hill, N.J.), 50 $\mu$g/ml endothelial cell growth supplement (Collaborative Research Incorporated, Bedford, Mass.), 25 mM Hepes Buffer, 2 mM L-glutamin, 100 $\mu$g/ml penicillin and 100 $\mu$g/ml streptomycin and grown at 37° C. on tissue culture plates coated 0.1% gelatin. Cells were passaged at confluency by splitting 1:4. Cells were used within the first 8 passages.

Incubation with Cytokines and Other Reagents Confluent HUVE cells were washed with phosphate buffered saline and then received fresh media. The indicated concentrations of PDTC were added as pretreatment 30 minutes before adding cytokines. Cytokines and other inducers were directly added to medium for the times and at the concentrations indicated in each experiment. Human recombinant IL-1b was the generous gift of Upjohn Company (Kalamazoo, Mich.). TNFa was obtained from Bohringer Engelheim. Bacterial lipopolysaccharide (LPS), polyinosinic acid: polycitidilic acid (Poly I:C), and pyrrolidine dithiocarbamate (PDTC) were obtained from Sigma Chemical (St. Louis, Mo.). All other reagents were of reagent grade.

RNA Isolation: Total cellular RNA was isolated by a single extraction using an acid guanidium thiocyanate-phenol-chloroform mixture. Cells were rinsed with phosphate buffered saline and then lysed with 2 ml of guanidium isothiocyanate. The solution was acidified with 0.2 ml of sodium acetate (pH 4.0) and then extracted with 2 ml phenol and 0.4 ml chloroform:isoamyl alcohol (24:1). The RNA underwent two ethanol precipitations prior to being used for Northern blot analysis.

Northern Blot Analysis: Total cellular RNA (20 $\mu$g) was size fractionated using 1% agarose formaldehyde gels in the presence of 1 ug/ml ethidium bromide. The RNA was transferred to a nitrocellulose filter and covalently linked by ultraviolet irradiation using a Stratlinker UV crosslinker (Stratagene, La Jolla, Calif.). Hybridizations were performed at 42° C. for 18 hours in 5×SSC (1×=150 mM NaCl, 15 mM Na citrate), 1% sodium dodecyl sulfate, 5×Denhardt solution, 50% formamide, 10% dextran sulfate and 100 ug/ml of sheared denatured salmon sperm DNA. Approximately 1–2×10$^6$ cpm/ml of labeled probe (specific activity>108 cpm/ug DNA) were used per hybridization. Following hybridization, filters were washed with a final stringency of 0.2×SSC at 55° C. The nitrocellulose was stripped using boiled water prior to rehybridization with other probes. Autoradiography was performed with an intensifying screen at −70° C.

$^{32}$Probes: $^{32}$P labeled DNA probes were made using the random primer oligonucleotide method. The ICAM-1 probe was an Eco R1 fragment of human cDNA. The ELAM-1 probe was a 1.85 kb Hind III fragment of human cDNA. The VCAM-1 probe was a Hind III-Xho I fragment of the human cDNA consisting of nucleotide 132 to 1814.

Enzyme Linked Immunosorbent Assay (ELISA): HUVE cells were plated on 96-well tissue culture plates 48 to 72 hours before the assay. Primary antibodies in M199 with 5% FBS were added to each well and incubated one hour at 37° C. The cells were then washed and incubated for one hour with peroxidase conjugated goat anti-mouse IgG (Bio Rad) diluted 1/500 in M199 with 5% FBS. The wells were then washed and binding of antibody was detected by the addition of 100 $\mu$l of 10 mg/ml 3,3,5,5'-tetramethyl-benzidine (Sigma) with 0.003% H$_2$O$_2$. The reaction was stopped by the addition of 25 $\mu$l of 8N sulfuric acid. Plates were read on an ELISA reader (Bio Rad) at OD 450 nm after blanking on rows stained only with second step antibody. Data represent the means of triplicate.

Antibodies: Monoclonal antibody (MAb) 4B9 recognizing vascular cell adhesion molecule-1 (VCAM-1) was the generous gift of Dr. John Harlan (University of Washington). MAb E9A1F1 recognizing endothelial cell adhesion molecule (ELAM-1) was the generous gift of Dr. Swerlick (Emory University). Hybridomas producing mAb 84H$_{10}$ recognizing intercellular adhesion molecule 1 (ICAM-1) are routinely grown in our laboratory and antibody was used as tissue culture supernatant.

EXAMPLE 9

Figure 10A:
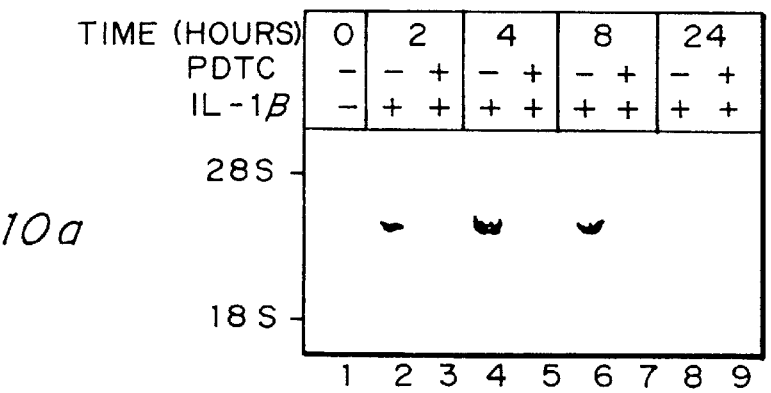
FIG. 10 is an illustration of an autoradiogram of mRNA, obtained as described below, hybridized to either 32P-labeled human VCAM-1 specific cDNA (Panel A), E-selectin (ELAM-1) specific cDNA (Panel B), or ICAM-1 specific CDNA (Panel C). Following pre-treatment for 30 minutes with 50 $\mu$M of sodium pyrrolidine dithiocarbamate (PDTC), HUVE (human umbilical vein) cells were exposed to IL-1b (10 U/ml) in the continuous presence of 50 $\mu$M PDTC. Parallel controls were performed identically except in the absence of PDTC. At the indicated times, total RNA was isolated and 20 $\mu$g of material size-fractionated by denaturing 1.0% agarose-formaldehyde gel electrophoresis, transferred to nitrocellulose, hybridized as described above, and visualized by autoradiography. Lane 1-0 hour; Lanes 2,4,6,8-OL-1 alone for 2, 4, 8 and 24 hours, respectively; Lanes 3,5,7,9-IL-1 with PDTC for 2,4,8 and 24 hours, respectively.
Figure 10B:
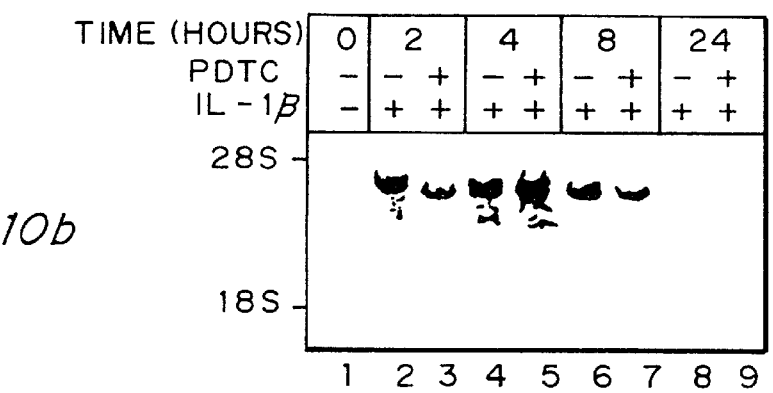
Figure 10C:
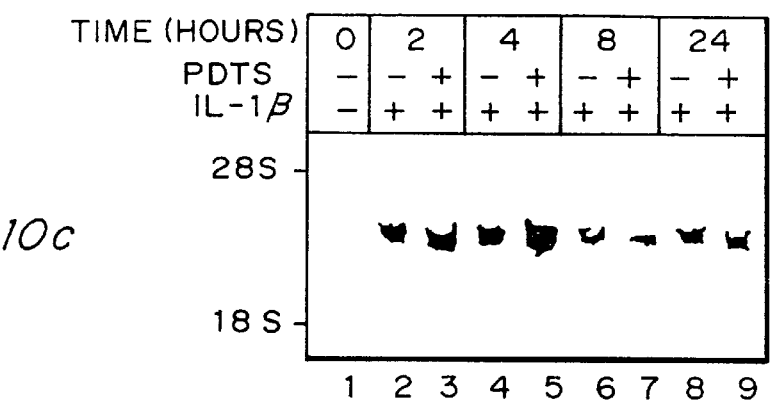

PDTC Blocks IL-1b Mediated Induction of HUVEC VCAM-1, but not ICAM-1 or ELAM-1, mRNA Accumulation To determine whether the oxidative state of the endothelial cell can alter the basal or induced expression of cell adhesion molecule genes, cultured human vascular endothelial cells were exposed to the inducing cytokine, IL-1b (10 U/ml) in the presence or absence of the thiolated metal chelating antioxidant, pyrrolidine dithiocarbamate (PDTC, 50 $\mu$M) for up to 24 hours. As shown in FIG. 10, IL-1b alone (lanes 2, 4, 6, 8) induces the expected rapid and transient induction of VCAM-1 (Panel A), E-selectin (ELAM-1, Panel B) and ICAM-1 (Panel C) mRNA accumulation, all of which peak at four hours. However, in the presence of PDTC, IL-1b induction of VCAM-1 mRNA accumulation is dramatically inhibited by over 90% (panel A, lanes 3, 5, 7, 9). In contrast, although IL-1b mediated induction of ELAM-1 is slightly inhibited at 2 and 24 hours (compare lane 2 and 3, 8 and 9, panel B), PDTC does not inhibit the induction at 4 and 8 hours (lane 5 and 7, panel B). IL-1b mediated induction of ICAM-1 mRNA accumulation is not affected (panel B, lanes 3, 5, 7, 9). Indeed, a mild augmentation of IL-1b induction of ICAM-1 mRNA accumulation (~30%) is observed (compare lanes 4 and 5, panel B). Equivalent amounts of nitrocellulose transferred RNA per lane was confirmed by ethidium bromide staining and visualization.

Figure 11A:
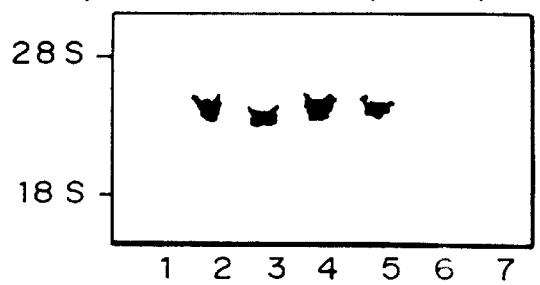
FIG. 11 is an illustration of an autoradiogram of mRNA, obtained as described below, hybridized to either 32P-labeled human VCAM-1 specific (Panel A), E-selectin (ELAM-1) specific CDNA (Panel B), or ICAM-1 specific CDNA (Panel C). HUVE cells were pretreated with the indicated concentrations of PDTC, and then exposed to IL-1b in the presence of PDTC for four hours and assayed for VCAM-1 mRNA accumulation by Northern filter hybridization analysis. Lane 1-control, lane 2-IL-1 (10 u/ml), lane 3-IL-1b+PDTC (0.05 $\mu$M), lane 4-IL-1 LB+PDTC (0.5 $\mu$M), lane 5-IL-1b+PDTC (5.0 $\mu$M), lane 6-IL=1b+PDTC (50.0 $\mu$M), lane 7-IL-1b+PDTC (100 $\mu$M).
Figure 11B:
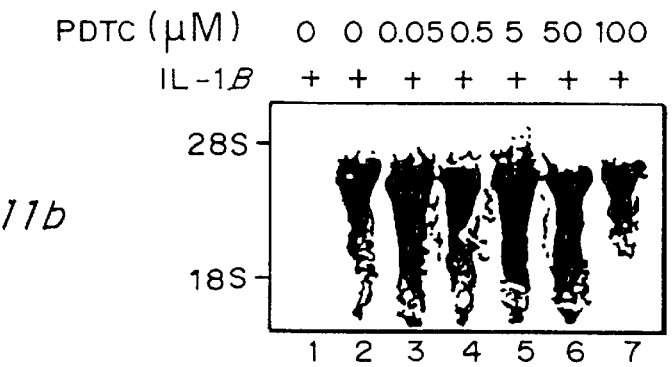
Figure 11C:
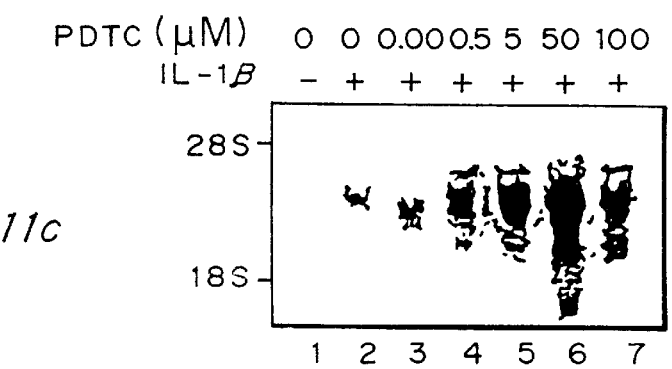

A dose-response analysis was performed to determine whether PDTC inhibits the induction of VCAM-1 gene expression by IL-1b in a dose dependent manner. As shown in FIG. 11, POTC inhibits IL-1b mediated induction of VCAM-1 gene expression with a steep dose-response curve (FIG. 11, panel A) with a calculated $EC_5$ of approximately 10 $\mu$M, while PDTC does not inhibit IL-1b mediated induction of ELAM-1 expression with these concentrations (FIG. 11, panel B). The IL-1b mediated induction of ICAM-1 mRNA accumulation is enhanced by PDTC with the concentration higher than 0.5 $\mu$M (FIG. 2, compare lane 2 and lane 4–7, panel C).

These data demonstrate that IL-1b utilizes a dithiocarboxylate, and in particular, a dithiocarbamate sensitive step as part of its signaling mechanism in the induction of VCAM-1 gene expression. The data also appear to indicate that this dithiocarbamate sensitive step does not play a significant role in the IL-1b mediated induction of ELAM-1 or ICAM-1 gene expression.

EXAMPLE 10

PDTC Blocks Induction of HUVEC VCAM-1 mRNA Accumulation by Multiple Stimuli

Figure 12A:
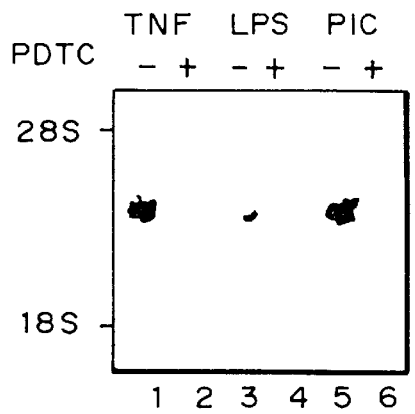
FIG. 12 is an illustration of an autoradiogram of mRNA, obtained as described below, hybridized to either 32P-labeled human VCAM-1 specific cDNA (Panel A), E-selectin (ELAM-1) specific cDNA (Panel B), or ICAM-1 specific cDNA (Panel C). HUVE cells were pretreated as described in FIG. 9 with 50 $\mu$M PDTC, exposed for four hours to the agents indicated below, and assayed for VCAM-1 (Panel A) and ICAM-1 (Panel B) mRNA accumulation. Lane 1-TNFa (100 U/ml), lane 2-TNFa+PDTC, lane 3-lipopolysaccharide (LPS) (100 ng/ml), lane 4-LPS+ PDTC, lane 5-poly(I:C) (100 mg/ml), lane 6-poly(I:C)+ PDTC.
Figure 12B:
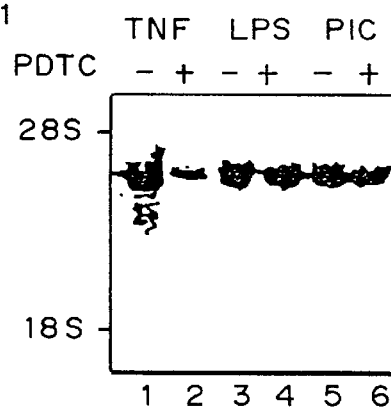
Figure 12C:
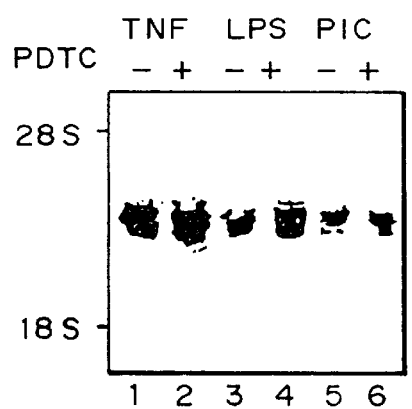

To determine whether other well-described activators of VCAM-1 gene expression also utilize a PDTC sensitive step, three distinct classes of activators were tested: another classic receptor mediated inducing agent (TNFa), a non-receptor mediated inducer (lipopolysaccharide (LPS)) and a recently described novel inducer (double stranded RNA, poly(I:C)). In all three cases, PDTC dramatically inhibited the induction of VCAM-1 mRNA accumulation in HUVECs after four hours (FIG. 12, Panel A). Although the TNFa mediated ELAM-1 gene expression is suppressed to some extent (FIG. 12 lane 1 and 2, panel B), LPS and poly(I:C) mediated ELAM-1 mRNA accumulation was unaffected (FIG. 12 lane 3–6, panel B). The induction of ICAM-1 mRNA accumulation was unaffected (FIG. 12, Panel C). This data indicates that structurally distinct inducing agents, acting through distinct pathways, share a common regulatory step specific for the induction of VCAM-1 gene expression.

EXAMPLE 11

PDTC Blocks HUVE Cell Surface Expression of VCAM-1 Induced by Multiple Stimuli

Figure 13A:
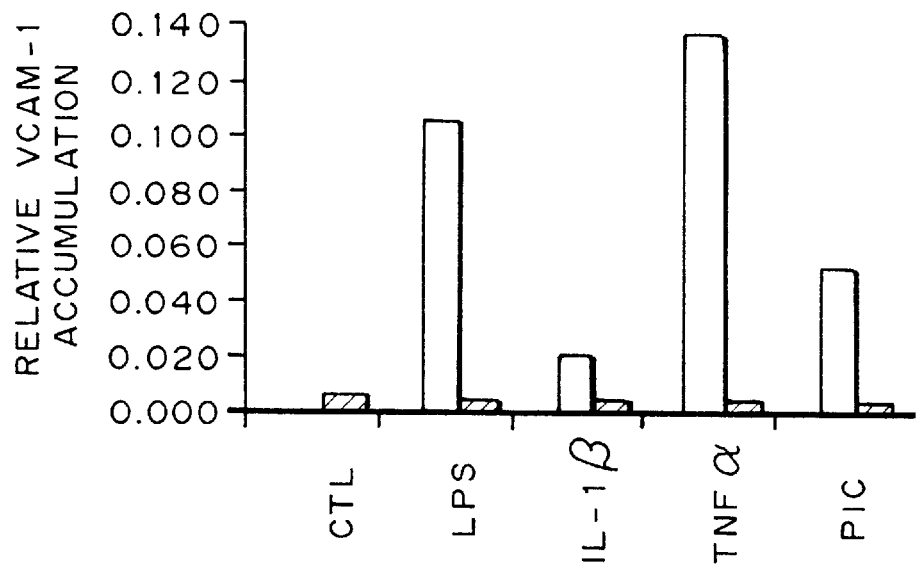
FIG. 13 is a graph of relative cell surface expression of VCAM-1 and ICAM-1 in the presence (dark bars) or absence (white bars) of PDTC and in the presence of multiple types of inducing stimuli. Confluent HUVECs were pretreated or not pretreated (CTL only) for 30 minutes with 50 μM PDTC, and then exposed for the indicated times to the indicated agents in the presence or absence (CTL only) of PDTC. Cell surface expression was determined by primary binding with VCAM-1 specific (4B9) and ICAM-1 specific (84H10) mouse monoclonal antibodies followed by secondary binding with a horse-radish peroxidase tagged goat anti-mouse (IgG). Quantitation was performed by determination of calorimetric conversion at 450 nm of TMB.
Figure 13B:
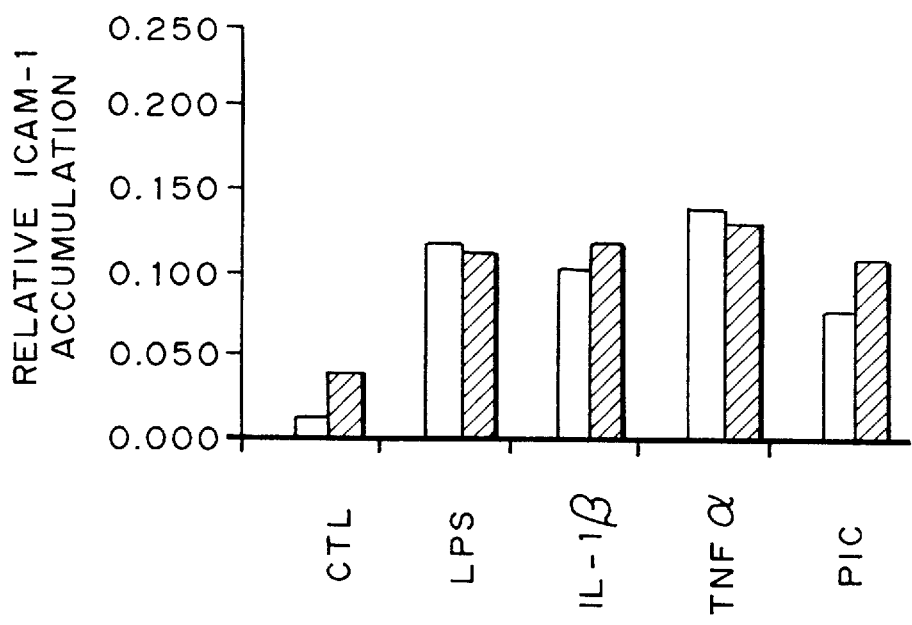

To determine whether, like its mRNA, the induction of endothelial cell surface protein expression of VCAM-1 could also be inhibited by PDTC, monoclonal antibodies were used in an ELISA assay to quantitate the induction of cell surface VCAM-1 and ICAM-1 in cultured HUVE cells. As shown in FIG. 13, multiple classes of activating agents, in the absence of PDTC (−PDTC), induce the rapid and transient accumulation of VCAM-1 (top left panel) at the cell surface peaking at six hours. In the presence of PDTC (+PDTC, top right panel), the induction of cell surface, expression of VCAM-1 by all agents tested is dramatically inhibited (80–90%). In contrast, the induced expression of cell surface ICAM-1 is unaffected under identical conditions (bottom left and right panels).

These data demonstrate that, like its mRNA accumulation, cell surface VCAM-1 expression are selectively inhibited by dithiocarbamates and that multiple classes of activating agents utilize a similar, dithiocarbamate sensitive mechanism to induce VCAM-1 gene expression.

EXAMPLE 12

Comparative Effectiveness of Antioxidants in Blocking TNFa Induction of VCAM-1

Figure 14:
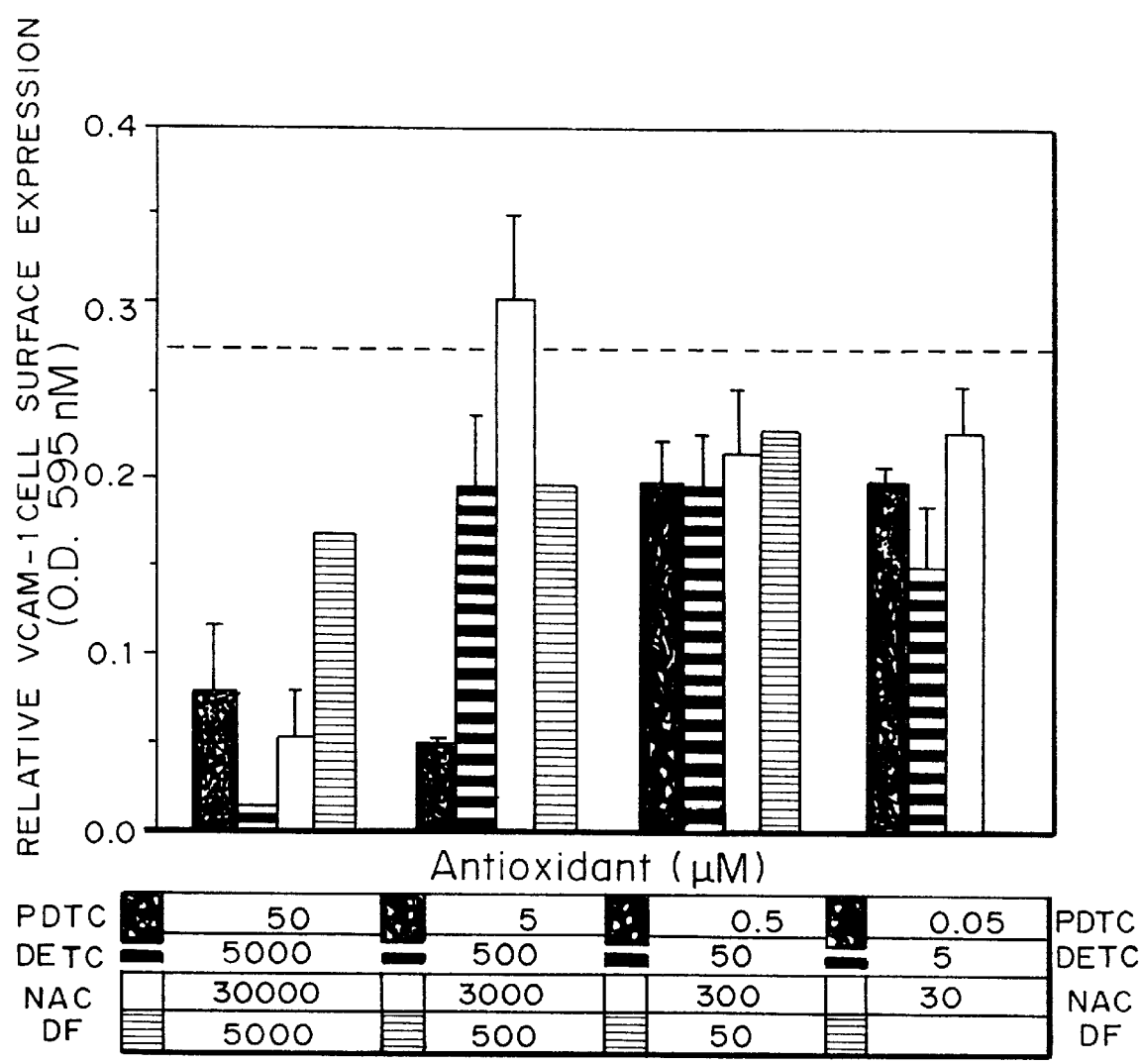
FIG. 14 is a graph of the relative VCAM-1 cell surface expression (O.D. 595 nM) in human umbilical vein endothelial cells, activated by TNFa, versus concentration of various antioxidants. (PDTC is sodium N-pyrrolidine dithiocarbamate; DETC is sodium N,N-diethyl-N-carbodithiolate, also referred to as sodium diethyldithiocarbamate; NAC is N-acetyl cysteine; and DF is desferroximine).

To determine whether structurally similar or dissimilar antioxidants could also inhibit VCAM-1 gene expression, and with what potency, HUVE cells were exposed to TNFa for six hours in the presence or absence of different concentrations of four different antioxidants. As shown in FIG. 14, both diethyldithiocarbamate (DETC) and N-acetyl cysteine (NAC) inhibited VCAM-1 expression at concentrations of 5 $\mu$M and 30 $\mu$M, respectively. In contrast, PDTC (PDTC) was effective between 5 and 50 $\mu$M. The iron metal chelator, desferroximine, had no effect at the concentrations tested.

EXAMPLE 13

PDTC Inhibits TNF Induction of VCAM-1/VLA-4 Mediated Adhesion

The ability of a variety of antioxidants to inhibit TNF-α induction of VCAM-1 in HUVE cells was evaluated by the method set out in Example 12. FIG. 15 is a graph of the relative VCAM-1 cell surface expression (O.D. 595 nM) in TNF-α activated HUVE cells versus concentrations of PTDC (sodium N-pyrrolidine dithiocarbamate), DIDTC (sodium N,N-diethyl-N-carbodithioate), SarDTC (sodium N-methyl-N-carboxymethyl-N-carbodithioate), IDADTC (trisodium N,N-di(carboxymethyl)-N-carbodithioate), MGDTC (sodium N-methyl-D-glucamine-N-carbodithioate), MeOBGDTC (sodium N-(4-methoxybenzyl)-D-glucamine-N-carbodithioate), DEDTC (sodium N,N-diethyl-N-carbodithioate), Di-PDTC (sodium N,N-diisopropyl-N-carbodithioate), and NAC is (N-acetyl cysteine).

EXAMPLE 13

PDTC Inhibits TNF Induction of VCAM-1/VLA-4 Mediated Adhesion

Figure 16A:
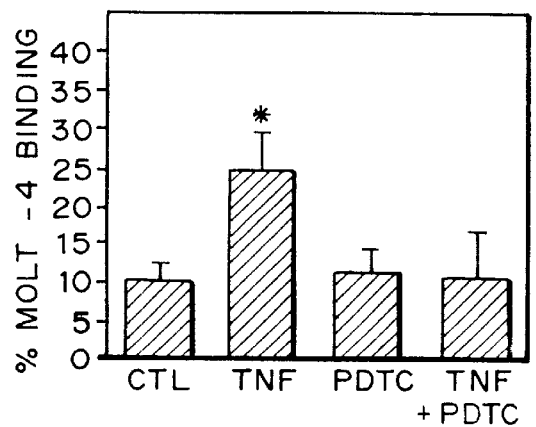
FIG. 16 is a graph of the percentage of Molt-4 cells binding to HUVE cells either unstimulated or stimulated with TNFa (100 U/mi) for six hours in the presence or absence of PDTC.
Figure 16B:
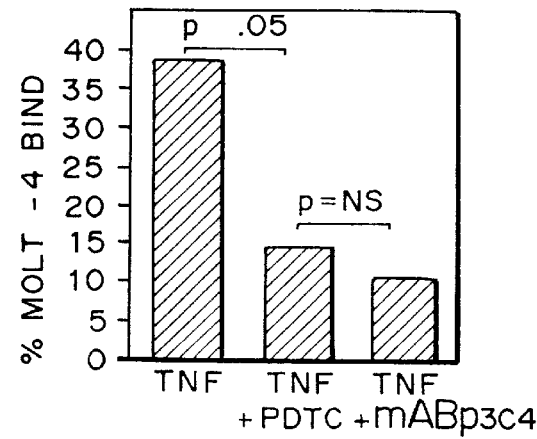

In order to define whether PDTC inhibition of VCAM-1 regulation is associated with functional consequences, the binding of Molt-4 cells to HUVEC cells either unstimulated or stimulated with TNFa (100 U/ml) was examined for six hours in the presence or absence of PDTC. Molt-4 cells have been previously shown to bind to activated HUVEC via a VCAM-1 dependent mechanism. As shown in FIG. 16, the percentage of Molt-4 binding to HUVEC cells decreased when PDTC was present in the media.

EXAMPLE 14

PDTC Inhibits Monocyte Binding to the Thoracic Aorta of Cholesterol Fed Rabbits

An experiment was performed to determine whether the thiol antioxidant PDTC would be efficacious in blocking the first monocyte binding component of atherosclerosis in an experimental animal model. One mature New Zealand white rabbit (3.5 Kg) received an intravenous injection of PDTC (20 mg/Kg, as a concentration of 20 mg/ml in PBS) once daily for 5 days. Injections were given via an indwelling cannula in the marginal ear vein, which as kept patent by flushing with heparinized saline solution. The PDTC solution was mixed fresh daily or on alternate days (stored light-protected at 4° C.), and filtered (0.45 mm pore filter) just prior to use. After the first injection, when the cannula was placed, the drug was administered with the rabbit in the conscious state without apparent discomfort or other ill effect. On the second day of injections, the rabbit was given chow containing 1% cholesterol by weight, which was continued throughout the remainder of the experiment. On the fifth day, the animal was euthanized and the thoracic aorta was excised and fixed. After appropriate preparation, the sample was imaged on the lower stage of an ISI DS-130 scanning electron microscope equipped with a LaB emitter. Using dual-screen imaging and a transparent grid on the CRT screen, 64 adjacent fields at a 620× magnification were assessed, to cover an area of ~1.3 mm². Within each field, the number of adherent leukocytes (WBC) and erythrocytes (RBC) were counted and recorded.

The data from the arch sample are as follows: 5 WBC and ~25 RBC per 1.3 mm² field. This level of WBC adhesion is similar to control animals fed regular chow (about 7 per field have been seen in arch and thoracic samples from 2 'negative control' experiments). 'Positive control' rabbits fed 1% cholesterol for 4 days but not given antioxidant show about a 5-fold increase in adhesion, to 38 WBC/1.3 mm². A considerable amount of mostly cell-sized debris was observed adherent to each arch sample. It is unclear whether this material is an artifact of preparation, or was present in vivo, and if so, whether it is related to PDTC administration. These studies suggest that PDTC infusions can effectively block initial monocyte adhesion to the aortic endothelium.

EXAMPLE 15

Inhibition of BSA 13-HPODE Adducts with PDTC

Figure 18:
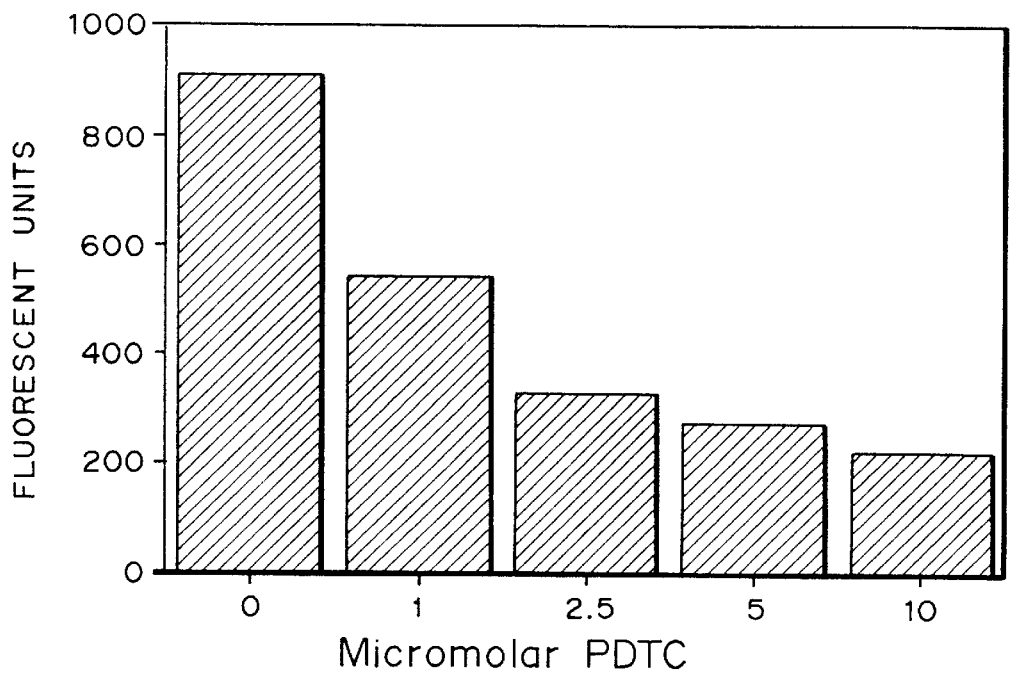
FIG. 18 is a bar chart graph of the effect of PTDC on the formation of fluorescent adducts of BSA and 13-HPODE, as measured in fluorescent units versus micromolar concentration of PDTC. One micromolar of 13-HPODE was incubated with 200 micrograms of BSA in the presence of PDTC for six days. Fluorescence was measured at 430–460 nm with excitation at 330–360 nm.

FIG. 18 is a bar chart graph of the effect of PTDC on the formation of fluorescent adducts of BSA and 13-HPODE, as measured in fluorescent units versus micromolar concentration of PDTC. One micromolar of 13-HPODE was incubated with 200 micrograms of BSA in the presence of PDTC for six days. Fluorescence was measured at 430–460 nm with excitation at 330–360 nm. For details of the assay, see Freebis, J., Parthasarathy, S., Steinberg, D, Proceedings of the National Academy of Sciences 89, 10588–10592, 1992. In a typical reaction 100 nmols of LOOH (generated by the lipoxygenase catalyzed oxidation of linoleic acid) in incubated with 100 µg of bovine serum albumin for 48 to 72 hours and the formation of fluorescent products are followed by measuring the fluorescent spectrum with excitation at 360 nm and emission between 390 and 500 nm.

As indicated, PDTC decreases the concentration of fluorescent adducts of BSA and 13-HPODE.

Figure 19:
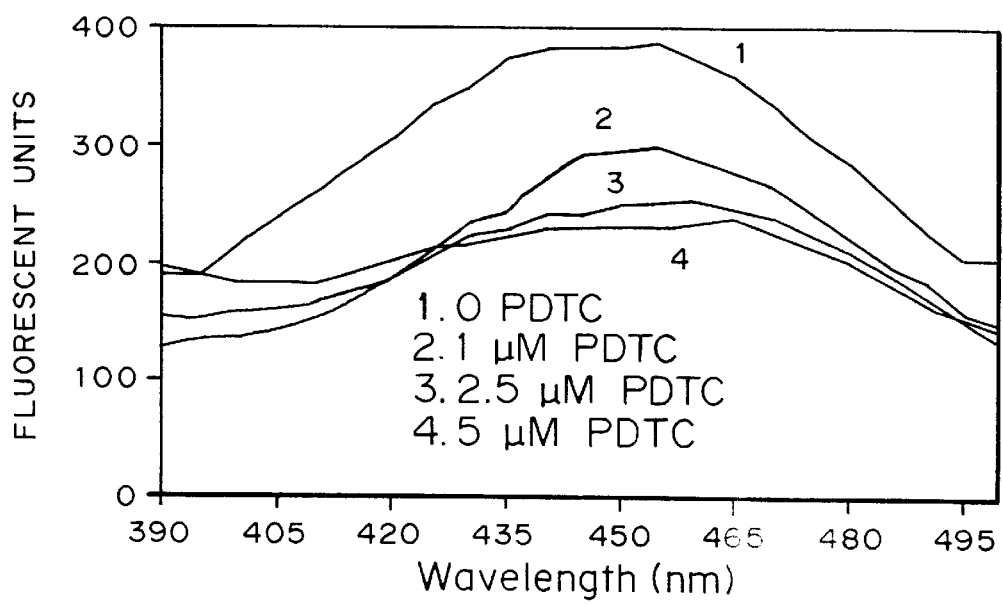
FIG. 19 is a graph of the effect of PTDC on the formation of fluorescent adducts of BSA and ox-PUFA as a function of wavelength (nm) and concentration of PDTC. As the concentration of PDTC increases, the quantity of fluorescent adducts decrease.

FIG. 19 is a graph of the effect of PTDC on the formation of fluorescent adducts of BSA and ox-PUFA as a function of wavelength (nm) and concentration of PDTC. As the concentration of PDTC increases, the quantity of fluorescent adducts decrease.

EXAMPLE 16

Effect of PDTC on the Oxidation of LDL by Horseradish Peroxidase

Figures 20, 21:
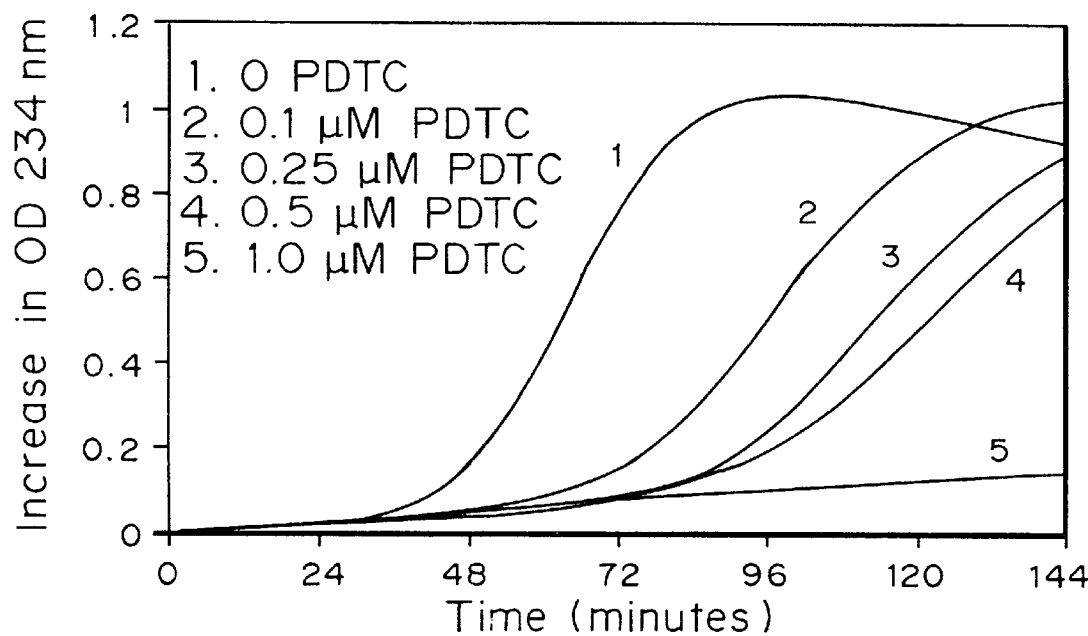
FIG. 20 is a graph of the effect of PDTC on the oxidation of LDL by horseradish peroxidase (HRP), as measured by the increase in O.D. (234 nm) versus time (minutes) for varying concentrations of PDTC. It is observed that after an incubation period, PDTC inhibits the oxidation of LDL by HRP in a manner that is concentration dependent.
FIG. 21 is a chart of the effect of PDTC on the cytokine-induced formation of ox-PUFA in human aortic endothelial cells. As indicated, both TNF-α and IL-1B causes the oxidation of linoleic acid to ox-linoleic acid. The oxidation is significantly prevented by PDTC.

FIG. 20 is a graph of the effect of PDTC on the oxidation of LDL by horseradish peroxidase (HRP), as measured over time (minutes) for varying concentrations of PDTC. The oxidation of LDL was followed by measuring the oxidation of the fatty acid components of LDL as determined by the increase in optical density at 234 nm. When a polyunsaturated fatty acid is oxidized, there is a shift of double bonds resulting in the formation of conjugated dienes which absorb at 234 nm. The intercept of the initiation and propagation curve (lag phase) is suggested to be a measure of the oxidizability of LDL. Higher the lag phase, more resistant is the LDL to oxidation. Typically 100 µg of human LDL is incubated with 5 µM $H_2O_2$ and the increase in absorption of 234 nm is followed.

It is observed that after an incubation period, PDTC inhibits the oxidation of LDL by HRP in a manner that is concentration dependent.

EXAMPLE 17

Effect of PDTC on the Cytokine-Induced Formation of ox-PUFA

FIG. 21 is a chart of the effect of PDTC on the cytokine-induced formation of ox-PUFA in human aortic endothelial cells. As indicated, both TNF-α and IL-1B causes the oxidation of linoleic acid to ox-linoleic acid. The oxidation is significantly prevented by PDTC.

2. Modification of the Synthesis and Metabolism of PUFAs and ox-PUFAs

Inhibition of the expression of VCAM-1 can be accomplished via a modification of the metabolism of PUFAs into ox-PUFAs. For example, a number of enzymes are known to oxidize unsaturated materials, including peroxidases, lipoxygenases, cyclooxygenases, and cytochrome P450. The inhibition of these enzymes may prevent the oxidation of PUFAs in vivo. PUFAs can also be oxidized by metal-dependent nonenzymatic materials.

IV. Method for Modifying the Expression of a Redox-Sensitive Gene

In an alternative embodiment, a method is provided for suppressing the expression of a redox-sensitive gene or activating a gene that is suppressed through a redox-sensitive pathway, that includes administering an effective amount of a substance that prevents the oxidation of the oxidized signal, and typically, the oxidation of a polyunsaturated fatty acid. Representative redox-sensitive genes that are involved in the presentation of an immune response include, but are not limited to, those expressing cytokines involved in initiating the immune response (e.g., IL-1β), chemoattractants that promote the migration of inflammatory cells to a point of injury (e.g., MCP-1), growth factors (IL-6, thrombin receptor), and adhesion molecules (e.g., VCAM-1 and E-selectin).

Given this disclosure, one of ordinary skill in the art will be able to screen a wide variety of antioxidants for their ability to suppress the expression of a redox-sensitive gene or activate a gene that is suppressed through a redox-sensitive pathway. All of these embodiments are intended to fall within the scope of the present invention.

Based on the results of this screening, nucleic acid molecules containing the 5' regulatory sequences of the redox-sensitive genes can be used to regulate or inhibit gene expression in vivo can be identified. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16), Furthermore, a number of viral and nonviral vectors are being developed that enable the introduction of nucleic acid sequences in vivo (see, e.g., Mulligan, 1993 *Science,* 260, 926–932; U.S. Pat. No. 4,980,286; U.S. Pat. No. 4,868,116; incorporated herein by reference). Recently, a delivery system was developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., 1993 *Science* 261, 209–211; incorporated herein by reference).

The 5' flanking sequences of the redox-sensitive gene can be used to inhibit the expression of the redox-sensitive gene. For example, an antisense RNA of all or a portion of the 5' flanking region of the redox-sensitive gene can be used to inhibit expression of the gene in vivo. Expression vectors (e.g., retroviral expression vectors) are already available in the art which can be used to generate an antisense RNA of a selected DNA sequence which is expressed in a cell (see, e.g., U.S. Pat. No. 4,868,116; U.S. Pat. No. 4,980,286). Accordingly, DNA containing all or a portion of the sequence of the 5' flanking region of the gene can be inserted into an appropriate expression vector so that upon passage into the cell, the transcription of the inserted DNA yields an antisense RNA that is complementary to the mRNA transcript of the gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the redox-sensitive gene to ensure that the antisense RNA contains complementary sequences present on the mRNA. Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280–284; Zamecnik et al., 1986 *Proc. Natl. Acad. Sci.,* 83, 4143–4146; Wickstrom et al., 1988 *Proc. Natl. Acad. Sci. USA* 85, 1028–1032; Crooke, 1993 *FASEB J.* 7, 533–539. Furthermore, recent work has shown that improved inhibition of expression of a gene by antisense oligonucleotides is possible if the antisense oligonucleotides contain modified nucleotides (see, e.g., Offensperger et. al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications); incorporated herein by reference).

The sequences of the 5' flanking region of the redox-sensitive gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., *Science* 245, 725–730; Orson et al., 1991 *Nucl. Acids Res.* 19, 3435–3441; Postal et al., 1991 *Proc. Natl. Acad. Sci. USA* 88, 8227–8231; Cooney et al., 1988 *Science* 241, 456–459; Young et al., 1991 *Proc. Natl. Acad. Sci. USA* 88, 10023–10026; Duval-Valentin et al., 1992 *Proc. Natl. Acad. Sci. USA* 89, 504–508; 1992 Blume et al., *Nucl. Acids Res.* 20, 1777–1784; 1992 Grigoriev et al., *J. Biol. Chem.* 267, 3389–3395.

Recently, both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., 1988 *Mol. Cell. Biol.* 8, 963–973; Wickstrom et al., 1988 *Proc. Natl. Acad. Sci. USA* 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.,* 65, 610–620 (1980) (phosphotriester method). Accordingly, DNA sequences of the 5' flanking region of the redox-sensitive gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of a redox-sensitive gene in order to inhibit expression of the gene.

In some cases it may be advantageous to insert enhancers or multiple copies of the regulatory sequences into an expression system to facilitate screening of methods and reagents for manipulation of expression.

V. Models and Screens

Screens for disorders mediated by VCAM-1 or a redox-sensitive gene are also provided that include the quantification of surrogate markers of the disease. In one embodiment, the level of oxidized polyunsaturated fatty acid, or other appropriate markers, in the tissue or blood, for example, of a host is evaluated as a means of assessing the "oxidative environment" of the host and the host's susceptibility to VCAM-1 or redox-sensitive gene mediated disease.

In another embodiment, the level of circulating or cell-surface VCAM-1 or other appropriate marker and the effect on that level of administration of an appropriate antioxidant is quantified.

In yet another assay, the sensitization of a host's vascular endothelial cells to polyunsaturated fatty acids or their oxidized counterparts is evaluated. This can be accomplished, for example, by challenging a host with a PUFA or ox-PUFA and comparing the resulting concentration of cell-surface or circulating VCAM-1 or other surrogate marker to a population norm.

In another embodiment, in vivo models of atherosclerosis or other heart or inflammatory diseases that are mediated by VCAM-1 can be provided by administering to a host animal an excessive amount of PUFA or oxidized polyunsaturated fatty acid to induce disease. These animals can be used in clinical research to further the understanding of these disorders.

In yet another embodiment of the invention, compounds can be assessed for their ability to treat disorders mediated by VCAM-1 on the basis of their ability to inhibit the oxidation of a polyunsaturated fatty acid, or the interaction of a PUFA or ox-PUFA with a protein target.

This can be accomplished by challenging a host, for example, a human or an animal such as a mouse, to a high level of PUFA or ox-PUFA and then determining the therapeutic efficacy of a test compound based on its ability to decrease circulating or cell surface VCAM-1 concentration. Alternatively, an in vitro screen can be used that is based on the ability of the test compound to prevent the oxidation of a PUFA, or the interaction of a PUFA or ox-PUFA with a protein target in the presence of an oxidizing substance such as a metal, for example, copper, or an enzyme such as a peroxidase, lipoxygenase, cyclooxygenase, or cytochrome P450.

In another embodiment, vascular endothelial cells are exposed to TNF-α or other VCAM-1 inducing material for an appropriate time and then broken by any appropriate means, for example by sonication or freeze-thaw. The cytosolic and membrane compartments are isolated. Radiolabeled PUFA is added to defined amounts of the compartments. The ability of the liquid to convert PUFA to ox-PUFA in the presence or absence of a test compound is assayed. Intact cells can be used in place of the broken cell system.

III. Pharmaceutical Compositions

Humans, equine, canine, bovine and other animals, and in particular, mammals, suffering from cardiovascular disorders, and other inflammatory conditions mediated by VCAM-1 or a redox sensitive gene can be treated by administering to the patient an effective amount of a compound that causes the removal, decrease in the concentration of, or prevention of the formation of an oxidized polyunsaturated fatty acids, including but not limited to oxidized linoleic ($C_{18}\Delta^{9,12}$), linolenic ($C_{18}\Delta^{6,9,12}$), arachidonic ($C_{20}\Delta5,8,11,14$) and eicosatrienoic ($C_{20}\Delta^{8,11,14}$) acids; other oxidation signal; or other active compound, or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethylammonium, or ethylenediamine; or (c) combinations of (a) and (b); e.g., a zinc tannate salt or the like.

The active compound or a mixture of the compounds are administered in any appropriate manner, including but not limited to orally and intravenously. General range of dosage for any of the above-mentioned conditions will be from 0.5 to 500 mg/kg body weight with a dose schedule ranging from once every other day to several times a day.

The compounds can also be administered directly to the vascular wall using perfusion balloon catheters following or in lieu of coronary or other arterial angioplasty. As an example, 2–5 mL of a physiologically acceptable solution that contains approximately 1 to 500 μM of the compound or mixture of compounds is administered at 1–5 atmospheres pressure. Thereafter, over the course of the next six months during the period of maximum risk of restenosis, the active compounds are administered through other appropriate routes and dose schedules.

Relatively short term treatments with the active compounds are used to cause the "shrinkage" of coronary artery disease lesions that cannot be treated either by angioplasty or surgery. A nonlimiting example of short term treatment is two to six months of a dosage ranging from 0.5 to 500 mg/kg body weight given at periods ranging from once every other day to three times daily.

Longer term treatments can be employed to prevent the development of advanced lesions in high-risk patients. A long term treatment can extend for years with dosages ranging from 0.5 to 500 mg/kg body weight administered at intervals ranging from once every other day to three times daily.

The active compounds can also be administered in the period immediately prior to and following coronary angioplasty as a means to reduce or eliminate the abnormal proliferative and inflammatory response that currently leads to clinically significant re-stenosis.

The active compounds can be administered in conjunction with other medications used in the treatment of cardiovascular disease, including lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal anti-inflammatories such as ibuprofen, indomethacin, fenoprofen, mefenamic acid, flufenamic acid, sulindac. The compound can also be administered with corticosteriods.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be administered with other active materials that do not impair the desired action, or with materials that supplement the desired action, such as antibiotics, antifungals, antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Suitable vehicles or carriers for topical application are known, and include lotions, suspensions, ointments, creams, gels, tinctures, sprays, powders, pastes, slow-release transdermal patches, aerosols for asthma, and suppositories for application to rectal, vaginal, nasal or oral mucosa.

Thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

The active compounds can be prepared with carriers that protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

If administered intravenously, preferred carriers are physiological saline or phosphate buffered saline (PBS).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221–229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Modifications and variations of the present invention will be obvious to those skilled in the art from the foregoing detailed description of the invention. Such modifications and variations are intended to come within the scope of the appended claims.

We claim:

1. A method for suppressing the expression of a redox-sensitive gene selected from the group consisting of MCP-1, IL-6 and thrombin receptor comprising administering an effective amount of a substance that prevents or minimizes the oxidation of a polyunsaturated fatty acid.

2. The method of claim 1, wherein the polyunsaturated acid is selected from the group consisting of oxidized linoleic ($C18\Delta^{9,12}$) acid and linolenic ($C_{18}\Delta^{6,9,12}$) acid.

3. The method of claim 1, wherein the polyunsaturated acid is selected from the group consisting of oxidized arachidonic ($C_{20}\Delta^{5,8,11,14}$) and eicosatrienoic ($C_{20}\Delta^{8,11,14}$) acid.

4. The method of claim 1, wherein the redox-sensitive gene is selected from the group consisting of those media the expression of expressing cytokines involved in initiating the immune response, chemoattractants that promote the migration of inflammatory cells to a point of injury, growth factors, and adhesion molecules.

5. The method of claim 1, wherein the substance is pyrrolidine dithiocarbamate, or its pharmaceutically acceptable salt.

6. The method of claim 1, wherein the substance is pyrrolidine dithiocarbamate, or its pharmaceutically acceptable salt.

7. The method of claim 1, wherein the gene mediates the expression of MCP-1.

8. The method of claim 1, wherein the gene mediates the expression of IL-6.

9. The method of claim 1, wherein the gene mediates the expression of thrombin receptor.

* * * * *